US008268789B2

(12) United States Patent
Kabeya et al.

(10) Patent No.: US 8,268,789 B2
(45) Date of Patent: Sep. 18, 2012

(54) PAR-2 ANTAGONISTS

(75) Inventors: Mototsugu Kabeya, Tokyo (JP); Kyoko Yasuoka, Tokyo (JP); Toru Kanke, Tokyo (JP); Hiroyuki Ishiwata, Chiba (JP); Junya Tagashira, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 818 days.

(21) Appl. No.: 11/576,304

(22) PCT Filed: Sep. 30, 2005

(86) PCT No.: PCT/JP2005/018145
§ 371 (c)(1),
(2), (4) Date: Jul. 15, 2008

(87) PCT Pub. No.: WO2006/035936
PCT Pub. Date: Apr. 6, 2006

(65) Prior Publication Data
US 2009/0012006 A1    Jan. 8, 2009

Related U.S. Application Data

(60) Provisional application No. 60/614,299, filed on Sep. 30, 2004.

(51) Int. Cl.
*A61K 38/06* (2006.01)
*A61K 38/02* (2006.01)
(52) U.S. Cl. ...................................... 514/21.9; 514/20.6
(58) Field of Classification Search .................... None
See application file for complete search history.

(56) References Cited

U.S. PATENT DOCUMENTS

| 5,888,529 | A | 3/1999 | Bunnett et al. |
| 5,958,407 | A | 9/1999 | Bunnett et al. |
| 7,056,942 | B2 * | 6/2006 | Hildesheim et al. .......... 514/411 |
| 2002/0103138 | A1 | 8/2002 | D'Andrea et al. |

FOREIGN PATENT DOCUMENTS

| JP | 2001-64203 A | 3/2001 |
| JP | 2001-181208 A | 7/2001 |
| JP | 2001-233790 A | 8/2001 |
| JP | 2003-286171 A | 10/2003 |
| WO | WO 03/049723 A2 | 6/2003 |
| WO | WO 03/049723 A3 | 6/2003 |
| WO | WO 03/104268 A1 | 12/2003 |
| WO | WO 2004/002418 A2 | 1/2004 |
| WO | WO 2004/002418 A3 | 1/2004 |

OTHER PUBLICATIONS

Vippagunta et al ('Crystalline solids' Adv. Drug Delivery Rev. v48 2001 pp. 3-26).*
Hingley ('Alzheimers: Few Clues on the mysteries of memory' retrieved from http://www.fda.gov/FDAC/features/1998/398_alz.html on Jan. 7, 2009 6 pages).*
Seattle Childrens hospital ('Colds' retrieved from http://www.seattlechildrens.org/medical-conditions/symptom-index/colds/ on Jan. 20, 2011 4 pages).*
World health organization ('Cancer prevention' retrieved from http://www.who.int/cancer/prevention/en/ on Jan. 20, 2011 2 pages).*
Goh et al (Dual effect of the novel peptide antagonist K-14585 on proteinase-activated receptor-2-mediated signalling British Journal of Pharmacology v158 2009 pp. 1695-1704).*
Web entry ('Summary of alkenes' retrieved from http://lsc.ucdavis.edu/~holliste/Jim118B/Ch-11.pdf on Jan. 20, 2011 1 page).*
Zhang et al ('Discovery and optimization of a novel series of thrombin receptor (PAR-1) antagonists: potent, selective peptide mimetics based on indole and indazole templates' J Med Chem 2001 44: pp. 1021-1024).*
Nystedt, S. et al.; Molecular Cloning of a Potential Proteinase Activated Receptor; Proceedings of the National Academy of Sciences USA, 91: pp. 9208-9212, 1994.
Molino, M. et al.; Interactions of Mast Cell Tryptase with Thrombin Receptors and PAR-2; The Journal of Biological Chemistry; vol. 272, pp. 4043-4049, 1997.
Camerer, E. et al.; Tissue factor- and factor X-dependent activation of protease-activated receptor 2 by factor Vlla; Proceeding of the National Academy of Sciences USA, 97; pp. 5255-5260, 2000.
Smith, R. et al; Evidence for the activation of PAR-2 by the sperm protease, acrosin: expression of the receptor on oocytes; FEBS Letters, 484, pp. 285-290, 2000.
Sawada, K. et al; Purification and Characterization of a Trypsin-Like Serine Proteinase from Rat Brain Slices that Degrades Laminin and Type IV Collagen and Stimulates Protease-Activated Receptor-2; Journal of Neurochemistry, 74; pp. 1731-1738, 2000.
Macfarlane, Scott R. et al.; Proteinase-Activated Receptors; Pharmacological Reviews, 53; pp. 245-282, 2001.
Kawabata, A. et al.; Increased vascular permeability by a specific agonist of protease-activated receptor-2 in rat hindpaw; Br J Pharmacology, 125; 419-422, 1998.
Nystedt, S. et al.; The Proteinase-activated Receptor 2 Is Induced by Inflammatory Mediators in Human Endothelial Cells; The Journal of Biological Chemistry, 271; pp. 14910-14915, 1996.
Ferrell, William R. et al; Essential role for proteinase activated receptor-2 in arthritis; J. Clin. Invest., 111; pp. 35-41, 2003.
Ohta, T. et al.; Protease-activated receptor-2 expression and the role of trypsin in cell proliferation in human pancreatic cancers; International Journal of Oncology, 23; pp. 61-66, 2003.

(Continued)

*Primary Examiner* — Cecilia J Tsang
*Assistant Examiner* — Ronald Niebauer
(74) *Attorney, Agent, or Firm* — Westerman, Hattori, Daniels & Adrian, LLP

(57) ABSTRACT

Compounds represented by the general formula (1) or salts thereof or solvates of both; PAR-2 antagonists containing the compounds; and preventive or therapeutic agents for PAR-2 related diseases containing the antagonists as the active ingredient: (1) wherein $R^1$ is hydrogen, halogeno, or a group represented by the general formula (2): (wherein $R^{11}$ is straight-chain or branched $C_{1-6}$ alkylene or the like; and $R^{12}$ and $R^{13}$ together with the nitrogen atom adjacent to them form a 5- to 7-membered ring); $R^2$ is straight-chain or branched $C_{1-6}$ alkyl or the like; $R^3$ and $R^4$ are each independently hydrogen, one to three halogen atoms, or the like; and $A^1$-$A^2$-$A^3$ is a tripeptide residue composed of α-amino acids each independently selected from the group consisting of glycine, alanine, cyclohexylalanine, and so on.

3 Claims, 1 Drawing Sheet

OTHER PUBLICATIONS

Lindner, Jonathan R. et al.; Delayed Onset of Inflammation in Protease-Activated Receptor-2-Deficient Mice; Journal of Immunology, 165; pp. 6504-6510, 2000.

Kong, W. et al.; Luminal trypsin may regulate enterocytes through proteinase-activated receptor 2; Proc. Natl. Acad. Sci. USA, 94; pp. 8884-8889, 1997.

Hawthorne, Susan J. et al.; A High-Throughput Microtiter Plate-Based Calcium Assay for the Study of Protease-Activated Receptor 2 Activation; Analytical Biochemistry, 290; pp. 378-379, 2001.

Hollenberg, Morley D. et al.; Proteinase-activated receptors; structural requirements for activity, receptor cross reactivity, and receptor selectivity of receptor-activating peptides; Can. J. Physiol Pharmacol., 75; pp. 832-841, 1997.

Kawabata, A. et al.; Proteinase-activated receptor-2 (PAR-2): regulation of salivary and pancreatic exocrine secretion in vivo in rats and mice, 129; pp. 1808-1814, 2000.

Al-ani, B. et al.; Proteinase-Activated Receptor 2 ($PAR_2$): Development of a Ligand-Binding Assay Correlating with Activation of $PAR_2$ by $PAR_1$- and $PAR_2$- Derived Peptide Ligands[1]; The Journal of Pharamacology and Experimental Therapeutics, vol. 290; pp. 753-760, 1999.

Covic, L. et al.; Pepducin-based intervention of thrombin-receptor signaling and systemic platelet activation; Nature Medicine, vol. 8; pp. 1161-1165, 2002.

Translation of International Preliminary Report on Patentability mailed Apr. 12, 2007 of International Application No. PCT/JP2005/018145.

Translation of International Preliminary Report on Patentability mailed Apr. 12, 2007 of International Application No. PCT/JP2005/018146.

Supplementary European Search Report dated Aug. 27, 2008, issued in corresponding European patent application No. 05788300.1.

Patricia Andrade-Gordon et al.; "Design, synthesis, and biological characterization of a peptide-mimetic antagonist for a tethered-ligand receptor"; Proc. Nat'l. Acad. Sci. USA, vol. 96, No. 22, pp. 12257-12262. Cited in the international search report, (1999).

Victor E Barrios et al.; "Proteinase-activated receptor-2 mediates hyperresponsiveness in isolated guinea pig bronchi"; Biochemical Pharmacology, vol. 66, No. 3, pp. 519-525, (2003). Cited in the international search report.

International Search Report of PCT/JP2005/018145, date of mailing Nov. 22, 2005.

* cited by examiner

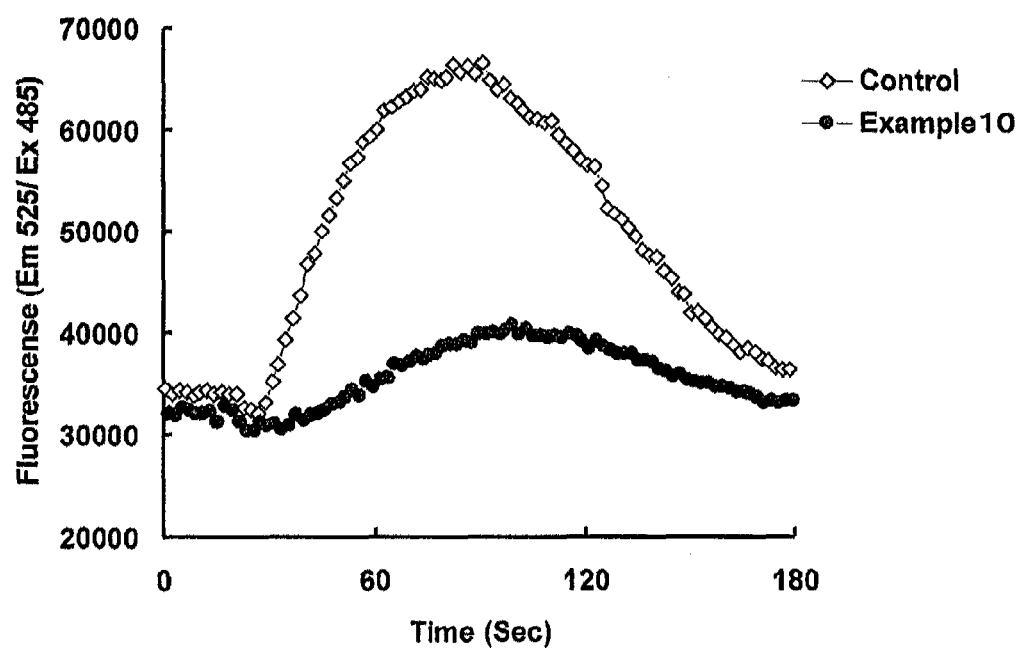

PAR-2 ANTAGONISTS

TECHNICAL FIELD

The present invention relates to a PAR-2 antagonist and a prophylactic/therapeutic agent for PAR-2-associated diseases, including the PAR-2 antagonist as an active ingredient and in particular to a pharmaceutical preparation useful for prevention of development and progress, amelioration of clinical state, treatment or the like for respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers.

BACKGROUND ART

PAR (Protease-Activated Receptor)-2 is a G protein-binding receptor of 7-times transmembrane type found in 1994 by Nystedt et al. (Proc Natl Acad Sci USA, 91, 9208-9212 (1994)). A protease activated receptor (PAR) family in which PAR-1, 2, 3, and 4 have been conventionally known has a unique activation mechanism wherein the activation of PAR is induced by cleaving a specific site in the extracellular N terminal of the receptor molecule, with the action of a protease such as thrombin or trypsin, and then binding a ligand site of the newly exposed cleavage terminal to a binding site of the receptor itself. PAR-1, 3, and 4 are known to be activated by thrombin, while PAR-2 is not activated by thrombin but activated by proteases such as trypsin (Proc Natl Acad Sci USA, 91, 9208-9212 (1994)), tryptase (J Biol Chem., 272(7): 4043-4049 (1997)), tissue factor/factor VIIa, factor Xa (Proc Natl Acad Sci USA., 97(10):5255-5260 (2000)), arccosine that is one type of sperm protease (FEBS Lett., 484(3):285-290 (2000)), and trypsin-like serine protease identified from a rat brain (J Neurochem., 74(4):1731-1738 (2000)).

PAR-2 is known to be distributed widely in endothelial tissues, is shown to be expressed at particularly high levels in digestive organs, respiratory organs, blood vessels, skin, kidney and the like, and is suggested to be likely to participate widely in inflammatory diseases because it is activated by trypsin, mast cell-derived tryptase or the like in a living body as described above (Pharmacological Rev, 53, 245-282, (2001)). Actually, pharmacological and genetic analysis in recent years using PAR-2 activating peptides or PAR-2 knockout mice have revealed that the stimulation of PAR-2 exhibits an inflammatory action on many organs (Br J Pharmacol, 125, 419-422 (1998)); the expression of PAR-2 is induced by inflammatory stimulation (J Biol Chem., 271(25): 14910-14915, (1996)); PAR-2 is expressed at high levels in inflammatory tissues, atherosclerotic plaques, cancer cells, or the like (J Clin Invest., 111(1):35-41, (2003), Int J Oncol., 23(1):61-66 (2003), or the like); in the PAR-2 knockout mice, a development of inflammations is suppressed in a contact dermatitis model or in an experimental arthritis model (International Publication WO03/049723) and topical infiltration of inflammatory cells causing asthma is suppressed (J Immunol., 165(11):6504-6510 (2000)) or the like, and the action of PAR-2 on inflammations and cancers attracts attention. Accordingly, it is estimated that the prevention of development and progress or amelioration of clinical state for inflammatory diseases (asthma, allergic rhinitis, atopic dermatitis, chronic arthritis and the like) and cancers is made feasible by inhibiting the activation of PAR-2, and the development of PAR-2 activation inhibitors, particularly PAR-2 antagonists, as novel anti-inflammatory agents and anticancer drugs is expected.

In the lacrimal gland and salivary gland, the significant secretion of lacrimal fluid and saliva by PAR-2 activation is recognized, and it is suggested that PAR-2 agonists can serve as therapeutic agents useful for diseases with a reduced secretion problem in the lacrimal gland and salivary gland, such as Sjogren's syndrome (Japanese Patent Application Laid-open Nos. 2001-64203 and 2001-181208). In the digestive organs, there are reports on the protective action, attributable to activation of PAR-2, on gastric mucosa (Japanese Patent Application Laid-open No. 2001-233790), and the promotion, by activation of PAR-2, of autonomic movement of the bowel (U.S. Pat. Nos. 5,888,529 and 5,958,407), and it is estimated that the activation of PAR-2 by PAR-2 agonists would be useful for treatment of gastric ulcer and intestinal obstruction.

As described above, the possibility of PAR-2-targeting agonists or antagonists as therapeutic agents attracts attention, and various methods for evaluation of PAR-2activation have been attempted. For example, the quantification of phosphorylated inositol (Proc Natl Acad Sci USA., 5;94(16): 8884-8889 (1997)) or the measurement of intracellular $Ca^{2+}$ level changes (Anal Biochem., 290(2):378-9 (2001)) has been generally used as a method of using for the production of second messenger accompanying the activation of PAR-2using cells expressing PAR-2. As a method of evaluating the activation ex vivo or in vivo, there are known a method of using the relaxation of an extirpated blood vessel as an indicator (Can J Physiol Pharmacol., 75(7):832-41 (1997)), a method of using salivary hypersecretion as an indicator (Br J Pharmacol., 129(8):1808-14 (2000)), or the like. As a method of directly evaluating the interaction between the ligand and G protein-binding receptor, a receptor-ligand binding test wherein the ligand is labeled with a radioisotope or a fluorescent dye is generally used. There are reports on a receptor-ligand binding test wherein PAR-2-specific ligand trans-cinnamoyl-LIGRLO (SEQ ID NO: 1)-$NH_2$ is used (J Pharmacol Exp Ther, 290, 753-760 (1999)) and on a high-sensitivity assay using highly active PAR-2-activating peptide 2-furoyl-LIGRL (SEQ ID NO: 2)-$NH_2$ (which is being contributed).

However, a report on PAR-2-selective highly active agonists (International Publication WO03/104268) is recognized as described above, but a report on compounds evidently having a PAR-2 antagonist activity is hardly recognized. Up to now, a compound inhibiting an intracellular signal transmission by stimulation with a PAR-2 agonist has been reported (Japanese Patent Application Laid-open No. 2003-286171), however whether the action of the compound is a direct inhibitory action on PAR-2, is not revealed. A series of antagonists described as being derived from PAR-2 agonist structures have been reported (International Publication WO2004/002418), however their inhibitory activity cannot be said to be satisfactory because the mechanism of PAR-2 inhibition is not revealed and further because the concentration thereof for inhibiting PAR-2 stimulation is shown to be in the order of mM. In addition to those described above, peptides derived from PAR-1 or PAR-2 activating peptides reported by Al-Ani et al. are reported to suppress the activation of PAR-2 by stimulation with trypsin, but do not exhibit an inhibitory effect on PAR-2 activating peptides, and are suggested to inhibit the binding or interaction between trypsin and PAR-2. As another unique method of inhibiting PAR-2 activation, there is an approach of specifically inhibiting the signal transmission by preventing the receptor from binding to G protein by using a compound (Pepducin) having palmitic acid added to a peptide mimicking an intracellular domain structure of PAR-2 receptor (Nat Med. 2002 October; 8(10):1161-5), but a use of this approach as pharmacotherapy still has a problem with respect to suitable delivery of the compound to a target site, specificity of receptor signal or the like.

Accordingly, the object of the present invention is to provide a PAR-2 antagonist acting competitively on a ligand-binding site of the receptor by inhibiting the activation of the PAR-2 accurately at the receptor level. That is, the object of the present invention is to provide a pharmaceutical preparation useful for prevention of development and progress, amelioration of clinical state, treatment or the like for PAR-2-associated diseases, for example, respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers.

DISCLOSURE OF INVENTION

In a view of the circumstances described above, the present inventors made extensive study and as a result, found that a compound represented by the general formula (1) or a salt thereof or a solvate thereof:

[Chemical formula 1]

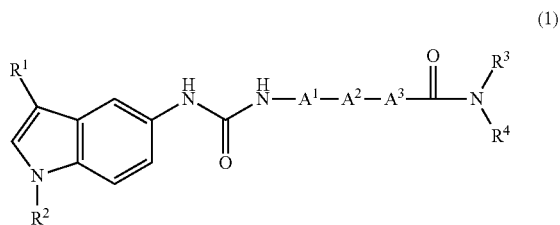

(1)

(wherein $R^1$ represents a hydrogen atom, a halogen atom, or a group represented by the following formula (2):

[Chemical formula 2]

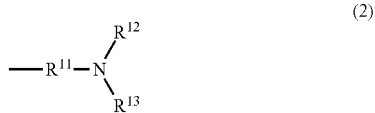

(2)

(wherein $R^{11}$ represents a $C_1$ to $C_6$ straight-chain or branched alkylene group, and $R^{12}$ and $R^{13}$ forms a 5- to 7-member ring structure together with the adjacent nitrogen atom, 1 to 2 carbon atoms in the ring may be substituted with a nitrogen atom or an oxygen atom, and the ring may be substituted with a $C_1$ to $C_6$ straight-chain or branched alkyl group;)

$R^2$ represents a $C_1$ to $C_6$ straight-chain or branched alkyl group, a $C_3$ to $C_6$ cycloalkyl group, a $C_1$ to $C_6$ straight-chain or branched alkyl group substituted with a $C_3$ to $C_6$ cycloalkyl group, or a $C_7$ to $C_{12}$ aralkyl group which may be substituted with to 3 halogen atoms or with a $C_1$ to $C_6$ straight-chain or branched alkyl group;

each of $R^3$ and $R^4$ independently represents a hydrogen atom or a $C_7$ to $C_{21}$ aralkyl group which may be substituted with 1 to halogen atoms or with a $C_1$ to $C_6$ straight-chain or branched alkyl group; and each of $A^1$-$A^2$-$A^3$ independently represents a tripeptide residue consisting of α-amino acids selected from the group consisting of glycine, alanine, cyclohexylalanine, α,γ-diaminobutyric acid, lysine, arginine, phenylalanine, valine, and naphthylalanine) strongly suppresses the signal transmission of human keratinocyte by PAR-2 agonist, and thus has an inhibitory effect on PAR-2.

Accordingly, the present invention provides the compound represented by the general formula (1), a salt thereof or a solvate thereof.

The present invention also relates to a pharmaceutical composition for prophylaxis and therapy of PAR-2-associated diseases, which includes a compound represented by the general formula (1), a salt thereof or a solvate thereof and a pharmaceutically acceptable carrier.

Further, the present invention relates to a pharmaceutical composition for prophylaxis and therapy of respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers, which comprises a compound represented by the general formula (1), a salt thereof or a solvate thereof and a pharmaceutically acceptable carrier.

Further, the present invention relates to a prophylactic/therapeutic method for PAR-2-associated diseases, which includes administering an effective amount of the compound (1) of the invention, a salt thereof or a solvate thereof to patients having, or likely to have, PAR-2-associated diseases.

Further, the present invention relates to a prophylactic/therapeutic method for respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers, which includes administering an effective amount of the compound (1) of the invention, a salt thereof or a solvate thereof to patients having, or likely to have, respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers.

Further, the present invention relates to a use of the compound (1) of the present invention, a salt thereof or a solvate thereof in producing a pharmaceutical composition for prophylaxis and therapy of PAR-2-associated diseases.

Further, the present invention relates to the use of the compound (1) of the invention, a salt thereof or a solvate thereof in producing a pharmaceutical composition for prophylaxis and therapy of respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers.

Further, the present invention relates to a compound represented by the general formula (3) or a salt thereof or a solvate thereof:

[Chemical formula 3]

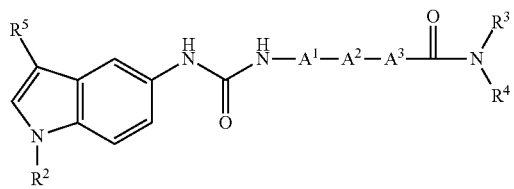

(3)

(wherein $R^5$ represents a halogen atom or —CO—$R^{51}$ (where $R^{51}$ represents a hydrogen atom, a $C_1$ to $C_6$ straight-chain or branched alkyl group, an optionally substituted phenyl group or an optionally substituted 2-furoyl group;)

$R^2$ represents a $C_1$ to $C_6$ straight-chain or branched alkyl group, a $C_3$ to $C_6$ cycloalkyl group, a $C_1$ to $C_6$ straight-chain or branched alkyl group substituted with a $C_3$ to $C_6$ cycloalkyl group, or a $C_7$ to $C_{12}$ aralkyl group which may be substituted with 1 to 3 halogen atoms or with a $C_1$ to $C_6$ straight-chain or branched alkyl group;

each of $R^3$ and $R^4$ independently represents a hydrogen atom or a $C_7$ to $C_{21}$ aralkyl group which may be substituted with 1 to 3 halogen atoms or with a $C_1$ to $C_6$ straight-chain or branched alkyl group; and each of $A^1$-$A^2$-$A^3$ independently represents a tripeptide residue consisting of α-amino acids selected from the group consisting of glycine, alanine, cyclohexylalanine, α,γ-diaminobutyric acid, lysine, arginine, phenylalanine, valine, and naphthylalanine.)

According to the present invention, there can be provided a PAR-2 antagonist which can serve as a prophylactic/therapeutic agent effective against various PAR-2-associated diseases including inflammatory diseases by inhibiting signal transmission via PAR-2.

BRIEF DESCRIPTION OF DRAWING

FIG. 1 shows an intracellular $Ca^{2+}$ level change by PAR-2 agonist in human keratinocytes expressing PAR-2, as well as an inhibitory action by PAR-2 antagonist.

BEST MODE FOR CARRYING OUT THE INVENTION

Hereinafter, the invention is described by reference to the general formulae (1) to (3).

In the general formula (1), the halogen atom represented by $R^1$, halogen atoms in the $C_7$ to $C_{12}$ aralkyl group which may be substituted with 1 to 3 halogen atoms, represented by $R^2$, and halogen atoms in the $C_7$ to $C_{21}$ aralkyl group which may be substituted with 1 to 3 halogen atoms, represented by $R^3$ and $R^4$, include a fluorine atom, a chlorine atom, a bromine atom and an iodine atom.

$R^1$ represents a hydrogen atom, a halogen atom, an optionally substituted pyrrolidinylmethyl group, an optionally substituted N-methylpiperazinylmethyl group, an optionally substituted morpholinylmethyl group or an optionally substituted 2-furoyl group, among which a hydrogen atom, a pyrrolidinylmethyl group and an N-methylpiperazinylmethyl group are preferable, and a pyrrolidinylmethyl group and an N-methylpiperazinylmethyl group are particularly preferable. Substituent groups on the pyrrolidinylmethyl group, N-methylpiperazinylmethyl group, morpholinylmethyl group and 2-furoyl group include a halogen atom, a hydroxyl group, a $C_1$ to $C_6$ straight-chain or branched alkyl group or a $C_3$ to $C_6$ cyclic alkyl group.

$R^2$ represents a halogen-substituted or unsubstituted benzyl group or a $C_1$ to $C_6$ straight-chain, branched or cyclic alkyl group, among which a halogen-substituted benzyl group and a $C_1$ to $C_6$ branched alkyl group are preferable, and 2,6-dichlorobenzyl group and an isopropyl group are particularly preferable.

Each of $R^3$ and $R^4$ independently represents a hydrogen atom or a $C_7$ to $C_{21}$ aralkyl group which may be substituted with 1 to 3 halogen atoms or with a $C_1$ to $C_6$ straight-chain or branched alkyl group, among which a hydrogen atom, a benzyl group and a benzhydryl group are particularly preferable.

Each of $A^1$-$A^2$-$A^3$ independently represents a tripeptide residue consisting of α-amino acids selected from the group consisting of natural or unnatural α-amino acids, preferably glycine, alanine, cyclohexylalanine, α,γ-diaminobutyric acid, lysine, arginine, phenylalanine, valine, and naphthylalanine.

The α-amino acid represented by $A^1$ is preferably glycine, alanine or cyclohexylalanine, more preferably glycine.

The α-amino acid represented by $A^2$ is preferably a $C_3$ to $C_8$ straight-chain diaminocarboxylic acid, more preferably α,γ-diaminobutyric acid or lysine.

The α-amino acid represented by $A^3$ is preferably phenylalanine, valine or β-naphthylalanine, more preferably phenylalanine.

The salt of the compound (1) of the present invention is not particularly limited insofar as it is a pharmaceutically acceptable salt, and preferable examples include acid addition salts, for example, mineral acid addition salts such as hydrochloride, hydrobromide, hydroiodide, sulfate and phosphate, and organic acid addition salts such as benzoate, methanesulfonate, ethanesulfonate, benzenesulfonate, p-toluenesulfonate, oxalate, maleate, fumarate, tartrate, citrate and acetate.

The compound (1) of the present invention can occur in the form of a solvate, typically including a hydrate, and the present invention also encompasses such solvate. When the compound (1) of the present invention has asymmetric carbon (s), the present invention also encompasses isomers of any configurations.

The compound represented by the general formula (1) in the present invention can be produced by a suitable combination of known chemical synthesis methods. In a preferable production process, for example, an α-amino acid in a free form or with its amino group protected is amidated, if necessary followed by deprotection of the amino group and if necessary conversion of the amino group into a reactive derivative, to produce an α-amino acid amide represented by the general formula (4):

[Chemical formula 4]

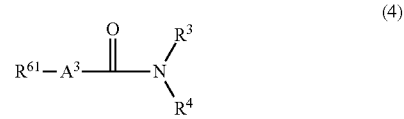

(4)

(wherein $R^3$, $R^4$, and $A^3$ have the same meanings as defined above, and $R^{61}$ represents a hydrogen atom, a protective group for amino group, or a group of a reactive derivative), followed by converting the product by a known peptide synthesis method into a tripeptide derivative represented by the general formula (5):

[Chemical formula 5]

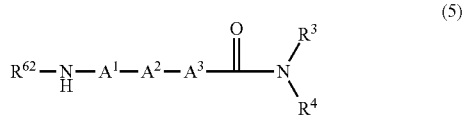

(5)

(wherein $R^3$, $R^4$ and $A^1$-$A^2$-$A^3$ have the same meanings as defined above, and $R^{62}$ represents a hydrogen atom, a protective group for amino group, or a reactive derivative), and then reacting the tripeptide derivative with a compound represented by the following general formula (6):

[Chemical formula 6]

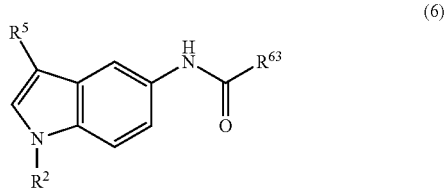

(6)

(wherein $R^2$ has the same meaning as defined above, $R^5$ has the same meaning as defined above or the same meaning as defined in $R^1$, and $R^{63}$ represents an eliminating group), whereby the compound represented by the general formula can be produced.

The compound represented by the general formula (1) in the present invention can be directly produced by the method described above; or alternatively the compound represented by the general formula (1) in the present invention can be obtained by producing an intermediate represented by the general formula (3):

[Chemical formula 7]

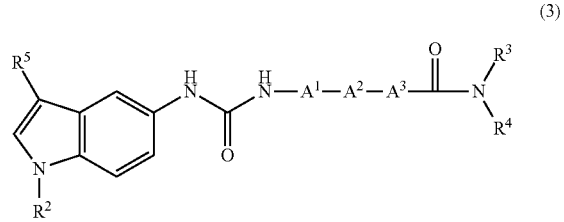

(3)

(wherein $R^5$ represents a halogen atom or —CO—$R^{51}$ (where $R^{51}$ represents a hydrogen atom, a $C_1$ to $C_6$ straight-chain or branched alkyl group, an optionally substituted phenyl group or an optionally substituted 2-furoyl group;)

$R^2$ represents a $C_1$ to $C_6$ straight-chain or branched alkyl group, a $C_3$ to $C_6$ cycloalkyl group, a $C_1$ to $C_6$ straight-chain or branched alkyl group substituted with a $C_3$ to $C_6$ cycloalkyl group, or a $C_7$ to $C_{12}$ aralkyl group which may be substituted with 1 to 3 halogen atoms or with a $C_1$ to $C_6$ straight-chain or branched alkyl group;

each of $R^3$ and $R^4$ independently represents a hydrogen atom or a $C_7$ to $C_{21}$ aralkyl group which may be substituted with 1 to 3 halogen atoms or with a $C_1$ to $C_6$ straight-chain or branched alkyl group; and each of $A^1$-$A^2$-$A^3$ independently represents a tripeptide residue consisting of α-amino acids each independently selected from the group consisting of glycine, alanine, cyclohexylalanine, α,γ-diaminobutyric acid, lysine, arginine, phenylalanine, valine, and naphthylalanine), and then subjecting this intermediate to known methods such as hydrolysis and amidation to form the compound of the general formula (1).

The intermediate represented by the general formula (3) in the present invention is a novel compound.

The process for producing the compound represented by the general formula (1) in the present invention will be described in more detail by reference to the Examples below.

The method of purifying the compound represented by the general formula (1) in the present invention includes usual purification means such as recrystallization and column chromatography. If necessary, the compound can be formed in a usual manner into the desired salt or solvate described above.

The pharmaceutical composition of the present invention includes the compound (1) of the present invention or a salt thereof or a solvate thereof as the active ingredient, and the administration form is not particularly limited and can be suitably selected depending on the therapeutic purpose, and the pharmaceutical composition can be for example an oral agent, an injection, a suppository, an ointment, an inhalant, eye drops, nasal drops, and an adhesive preparation, and the composition suitable for these administration forms can be produced by incorporating a pharmaceutically acceptable carrier into the active ingredient according to a preparation method known to those skilled in the art.

When an oral solid preparation is produced, tablets, coated tablets, granules, powder, capsules or the like can be produced in a usual manner after an excipient, if necessary a binder, a disintegrating agent, a lubricant, a coloring agent, a flavoring substance, a fragrant substance and the like are added to the compound (1) of the present invention. Such additives may be those generally used in the art; for example, the excipient includes lactose, sucrose, sodium chloride, glucose, starch, calcium carbonate, kaolin, microcrystalline cellulose, silicic acid and the like, the binder includes water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like, the disintegrating agent includes dry starch, sodium alginate, powdered agar, sodium hydrogen carbonate, calcium carbonate, sodium lauryl sulfate, monoglyceride stearate, lactose and the like, the lubricant includes purified talc, stearate, borax, polyethylene glycol and the like, and the flavoring substance includes sucrose, wild orange peel, citric acid, tartaric acid and the like.

When an oral liquid preparation is prepared, an oral liquid for internal use, a syrup, an elixir and the like can be produced in a usual manner by adding a flavoring substance, a buffer agent, a stabilizer, a fragrant substance and the like to the compound (1) of the present invention. In this case, the flavoring substance may be the one described above, and the buffer agent includes sodium citrate and the like, and the stabilizer includes tragacanth, gum arabic, gelatin and the like.

When the injection is prepared, subcutaneous, intramuscular and intravascular injections can be produced in a usual manner by adding a pH adjusting agent, a buffer agent, a stabilizer, a tonicity agent, a topical anesthetic agent or the like to the compound (1) of the present invention. In this case, the pH adjusting agent and the buffer agent include sodium citrate, sodium acetate, sodium phosphate and the like. The stabilizer includes sodium pyrosulfite, EDTA, thioglycolic acid, thiolactic acid and the like. The topical anesthetic agent includes procaine hydrochloride, lidocaine hydrochloride and the like. The tonicity agent can be exemplified by sodium chloride, glucose and the like.

When a suppository is prepared, it can be produced in a usual manner after pharmaceutical carriers known in the art, such as polyethylene glycol, lanolin, cacao seed oil, fatty acid triglyceride and the like and if necessary a surfactant such as Tween (registered trademark), are added to the compound (1) of the present invention.

When an ointment is prepared, it can be produced in a usual manner by blending and mixing the compound (1) of the present invention if necessary with usually used additives such as a base, a stabilizer, a moistening agent and a preservative. The base includes liquid paraffin, white petrolatum, Sarashi beeswax, octyldodecyl alcohol, paraffin and the like. The preservative includes methyl p-hydroxybenzoate, ethyl p-hydroxybenzoate, propyl p-hydroxybenzoate, and the like.

In addition to those described above, the compound (1) of the present invention can be formed in a usual manner into an inhalant, eye drops and nasal drops.

The amount of the active ingredient in the pharmaceutical composition of the invention administered varies depending on the age, sex, weight and symptom of the patient, therapeutic effect, treatment time, administration form, and administration frequency, and usually the compound (1) of the present invention is administered to an adult orally or parenterally in the range of 0.001 to 1000 mg, preferably 0.01 mg to 500 mg, all at once or in divided portions per day. However, the dose varies depending on various conditions, and thus a dose lower than the above dose may be sufficient in some cases or a dose higher than the above range may be necessary in other cases. For example, the injection can be produced by dissolving or suspending the compound (1) of the present invention at a concentration of 0.1 µg/mL to 10 mg/mL in a nontoxic pharmaceutically acceptable carrier such as physiological saline or commercial distilled water for injection.

The injection thus obtained can be administered in a dose of 1 µg to 100 mg, preferably 50 µg to 50 mg, for each administration, per body kg once to several times per day to a patient in need of treatment. The administration form can be exemplified by medically suitable administration forms such as intravenous injection, subcutaneous injection, intradermal injection, intramuscular injection and intraperitoneal injection. The intravenous injection is preferable. The injection can also be prepared as a suspension or emulsion with a non-aqueous diluent (for example, propylene glycol, polyethylene glycol and vegetable oils such as olive oil and alcohols such as ethanol) depending on the case. Sterilization of such injections can be carried out by filter sterilization, that is, through a bacteria-retaining filter, or with a sterilizer or through irradiation. The injection can be produced by a form for preparation just before use. That is, a germ-free solid composition is produced by lyophilization and can be dissolved in germ-free distilled water for injection or other solvent just before use.

The thus obtained pharmaceutical composition of the present invention has a selective inhibitory effect on PAR-2, as shown later in the Test Example, and is thus useful for prevention of development and progress, amelioration of clinical state, treatment and the like for PAR-2-associated diseases, for example, respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers. More specifically, the pharmaceutical composition of the present invention is useful for prevention of development and progress, amelioration of clinical state, treatment and the like for PAR-2-associated diseases such as emphysema, asthma, bronchitis, chronic obstructive lung disease, allergic reaction, allergic contact hypersensitivity, allergic rhinitis, atherosclerosis (atherosclerotic platelet destruction), aortic aneurysm (abdominal aortic aneurysm and cerebral aortic aneurysm), periarteritis nodosa, congestive heart failure, myocardial infarction, spasm, hypotension, shock, cerebral ischemia, head injury, spinal cord injury, neuralgia, neurodegenerative disease (acute and chronic), Alzheimer's disease, Huntington's chorea, Parkinson's disease, migraine headache, depression, peripheral neuropathy, pain (lower back and neck pain, headache and toothache), nerve tissue-derived neurogenic inflammation accompanied by pain, gingivitis, cerebral amyloid angiopathy, nootropic or recognition enhancement, arthritis (including osteoarthritis, degenerative arthritis, spondyloarthropathy, gouty arthritis, systemic lupus erythematosus, juvenile arthritis and chronic rheumatoid arthritis), fever (rheumatic fever and influenza and other viral infection-related fever), common cold, dysmenorrhea, menstrual cramp, inflammatory bowel disease, regional enteritis, ulcerative colitis, diverticulitis, recurrent gastrointestinal lesion, gastrointestinal hemorrhage, coagulation, anemia, synovial inflammation, gout, ankylosing spondylitis, restenosis, periodontal disease, epidermolysis bullosa, osteoporosis, loose of artificial joint implant, autoimmune disease, amyotrophic lateral sclerosis, multiple sclerosis, ocular angiopoiesis, corneal injury, yellow spot degeneration, conjunctivitis, abnormal wound healing, muscular or joint distortion or tension, tendonitis, cutaneous diseases (for example, psoriasis, eczema, scleroderma and dermatitis), myasthenia gravis, polymyositis, muscular inflammation, synovial bursitis, burn, diabetes mellitus (types I and II diabetes mellitus, diabetic retinopathy), tumor invasion, tumor growth, tumor metastasis, corneal scar, scleritis, immunodeficiency disorders (for example, human AIDS, feline FLV, FIV), sepsis, preterm delivery, hypoprothrombinemia, hemophilia, thyroiditis, sarcoidosis, Behcet's syndrome, hypersensitivity, Crohn's disease, organ transplantation toxicity, cachexia, and cancers (for example, solid tumors and cancers including colon cancer, breast cancer, lung cancer and prostate cancer; hematopoietic malignant diseases including leukemia and lymphoma; Hodgkins disease; aplastic anemia, skin cancer and familial adenomatous polyposis) and is particularly useful for prevention of development and progress, amelioration of clinical state, treatment and the like for asthma, bronchitis, chronic obstructive lung disease, allergic reaction, allergic contact hypersensitivity, allergic rhinitis, atherosclerosis, myocardial infarction, shock, cerebral ischemia, neuralgia, Alzheimer's disease, pain, nerve tissue-derived neurogenic inflammation accompanied by pain, arthritis, inflammatory bowel disease, regional enteritis, ulcerative colitis, synovial inflammation, immunodeficiency disorder, ocular vasculogenesis, conjunctivitis, abnormal wound healing, joint distortion or tension, skin disease, and cancers.

Hereinafter, the present invention is described in more detail by reference to the Examples, but the technical scope of the present invention is not limited to the Examples.

Hereinafter, t-butoxycarbonyl, 9-fluorenylmethoxycarbonyl and benzyloxycarbonyl are abbreviated sometimes as Boc, Fmoc and Z, respectively.

EXAMPLE 1

Production of Boc-Phe-CONHCHPh$_2$

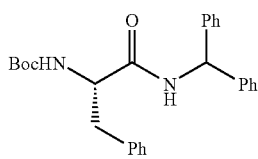

[Chemical formula 8]

61 mg (0.37 mmol) of diethylphosphorocyanidate was added to a solution of 66 mg (0.25 mmol) of N-α-t-butoxycarbonyl-L-phenylalanine, 68 mg (0.35 mmol) of benzhydryl amine and 96 mg (0.75 mmol) of N,N-diisopropyl ethylamine in anhydrous tetrahydrofuran (2 mL) under cooling on ice. After the mixture was stirred at room temperature for 16 hours, the reaction mixture was diluted with water and extracted with chloroform. The organic layer was washed with 1 N aqueous hydrochloric acid, saturated aqueous sodium bicarbonate and saturated saline and dried over anhydrous sodium sulfate, followed by distilling out the solvent, to give a crude oily material. The resulting oily material was purified by silica gel chromatography, whereby 107 mg of the title compound (yield 100%) was obtained as white crystalline powder.

$^1$H-NMR (CDCl$_3$) δ:
1.40 (s, 9H), 3.02 (dd, J=7.5, 13.9 Hz, 1H), 3.13 (dd, J=6.1, 13.9 Hz, 1H), 4.38 (br, 1H), 5.03 (br, 1H), 6.16 (br, 1H), 6.49 (d, J=8.0 Hz, 1H), 7.01 (bs, 2H), 7.12-7.19 (m, 4H), 7.21-7.32 (m, 9H)

EXAMPLE 2

Production of Phe-CONHCHPh$_2$·HCl

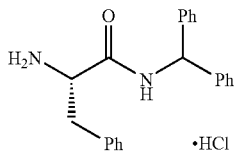

[Chemical formula 9]

2 mL (8 mmol) of 4 N hydrogen chloride in ethyl acetate was added to a solution of 104 mg (0.24 mmol) of N-α-t-butoxycarbonyl-L-phenylalanine-N-benzhydrylamide in dichloromethane (4 mL) under cooling on ice. Then, the mixture was stirred at room temperature for 2 hours and then concentrated under reduced pressure, and the residues were recrystallized from chloroform-ether, to give 89 mg of the title compound (yield 100%) as white crystalline powder.

$^1$H-NMR (CD$_3$OD) δ:
3.09-3.22 (m, 2H), 4.23 (t, J=7.5 Hz, 1H), 6.13 (s, 1H), 6.93-6.96 (m, 2H), 7.22-7.33 (m, 13H)

EXAMPLE 3

Production of N-α-Fmoc-N-ω-Boc-Lys-Phe-CONH-CHPh$_2$

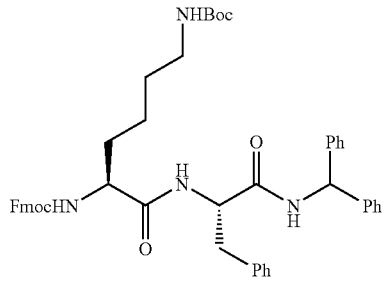

[Chemical formula 10]

By the same operation as in Example 1, 170 mg of the title compound (yield 91%) was obtained as white crystalline powder from 88 mg (0.24 mmol) of L-phenylalanine-N-benzhydrylamide hydrochloride and 157 mg (0.34 mmol) of N-α-(9-fluorenylmethoxycarbonyl)-N-ω-t-butoxycarbonyl-L-lysine.

$^1$H-NMR (CDCl$_3$+CD$_3$OD) δ:
1.16-1.27 (m, 2H), 1.35-1.44 (m, 2H), 1.44 (s, 9H), 1.50-1.70 (m, 2H), 3.00 (br, 2H), 3.00-3.17 (m, 2H), 4.03 (br, 1H), 4.12 (br, 2H), 4.31 (br, 1H), 4.67 (br, 1H), 6.15 (d, J=7.5 Hz, 1H), 7.02 (d, J=4.6 Hz, 2H), 7.07-7.27 (m, 15H), 7.28-7.36 (m, 2H), 7.41 (t, J=7.5 Hz, 2H), 7.49 (br, 1H), 7.52 (d, J=7.5 Hz, 1H), 7.57 (d, J=7.5 Hz, 1H), 7.77 (d, J=7.5 Hz, 2H)

EXAMPLE 4

Production of N-ω-Boc-Lys-Phe-CONHCHPh$_2$

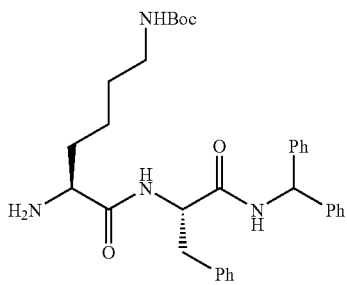

[Chemical formula 11]

2 mL (19 mmol) of diethylamine was added to a solution of 166 mg (0.21 mmol) of N-α-(9-fluorenylmethoxycarbonyl)-N-ω-t-butoxycarbonyl-L-lysine-L-phenylalanine-N-benzhydrylamide in tetrahydrofuran (6 mL). The mixture was stirred at room temperature for 16 hours and then concentrated under reduced pressure, and the resulting residues were recrystallized from chloroform-methanol-ether,to give 116 mg of the title compound (yield 98%) as white crystalline powder.

$^1$H-NMR (CDCl$_3$) δ:
1.10-1.25 (m, 2H), 1.30-1.55 (m, 2H), 1.44 (s, 9H), 1.55-1.70 (m, 2H), 3.04 (dd, J=7.5, 13.9 Hz, 2H), 3.01-3.07 (m, 1H), 3.16 (dd, J=7.3, 13.9 Hz, 1H), 3.27 (dd, J=4.6, 7.5 Hz, 1H), 4.51 (br, 1H), 4.68 (dd, J=7.5, 15.3 Hz, 1H), 6.14 (d, J=8.2 Hz, 1H), 6.93 (d, J=8.0 Hz, 1H), 7.03 (d, J=6.1 Hz, 2H), 7.16-7.30 (m, 11H), 7.14 (d, J=6.8 Hz, 2H), 7.83 (d, J=8.2 Hz, 1H)

EXAMPLE 5

Production of N-α-Fmoc-Gly-N-ω-Boc-Lys-Phe-CONHCHPh₂

[Chemical formula 12]

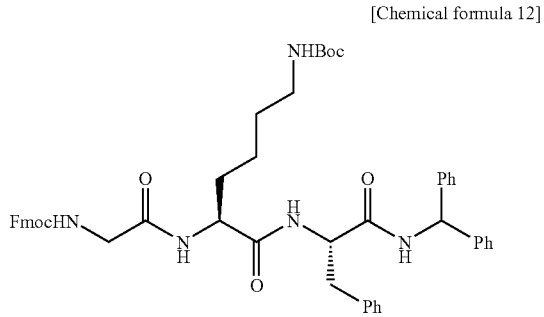

By the same operation as in Example 1, 162 mg of the title compound (yield 100%) was obtained as white solid from 80 mg (0.27 mmol) of N-α-(9-fluorenylmethoxycarbonyl)glycine and 108 mg (0.19 mmol) of N-ω-t-butoxycarbonyl-L-lysine-L-phenylalanine-N-benzhydryl amide.

¹H-NMR (CDCl₃) δ:

1.11 (br, 2H), 1.32-1.37 (m, 2H), 1.43 (s, 9H), 1.50-1.75 (m, 2H), 2.98 (br, 2H), 3.02 (dd, J=8.0, 13.6 Hz, 1H), 3.21 (br, 1H), 3.53-3.65 (m, 2H), 4.13-4.17 (m, 1H), 4.32 (br, 2H), 4.70 (q, J=7.8 Hz, 1H), 4.90 (br, 1H), 5.78 (br, 1H), 6.18 (d, J=7.8 Hz, 1H), 7.06 (d, J=6.5 Hz, 2H), 7.13-7.26 (m, 15H), 7.31 (dd, J=1.0, 7.5 Hz, 2H), 7.35 (br, 1H), 7.40 (t, J=7.5 Hz, 2H), 7.56 (t, J=8.0 Hz, 2H), 7.62 (br, 1H), 7.77 (d, J=7.5 Hz, 2H)

EXAMPLE 6

Production of Gly-N-ω-Boc-Lys-Phe-CONHCHPh₂

[Chemical formula 13]

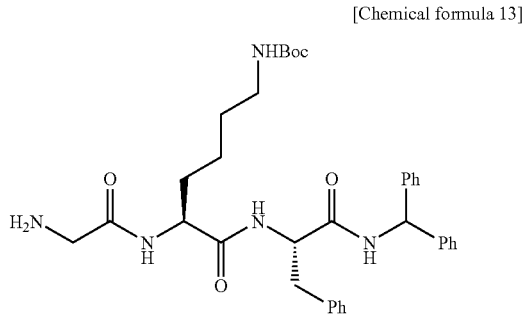

By the same operation as in Example 4, 50 mg of the title compound (yield 80%) was obtained as white solid from 85 mg (0.10 mmol) of N-α-(9-fluorenylmethoxycarbonyl) glycine-N-ω-t-butoxycarbonyl-L-lysine-L-phenylalanine-N-benzhydrylamide and 1 mL (9.57 mmol) of diethylamine.

¹H-NMR (DMSO-d₆, 120° C.) δ:

1.16-1.30 (m, 2H), 1.30-1.43 (m, 2H), 1.39 (s, 9H), 1.43-1.68 (m, 2H), 2.80-2.19 (m, 2H), 3.08 (dd, J=5.6, 13.6 Hz, 1H), 3.16 (s, 2H), 4.21 (dd, J=5.8, 8.0 Hz, 1H), 4.67 (dt, J=5.8, 8.0 Hz, 1H), 6.07 (d, J=8.5 Hz, 2H), 7.13-7.32 (m, 16H), 7.62 (d, J=8.0 Hz, 1H), 8.22 (d, J=8.0 Hz, 1H)

EXAMPLE 7

Production of 5-phenyloxycarbonylamino-N-[(1-(2,6-dichlorophenyl)-methyl]-1H-indole

[Chemical formula 14]

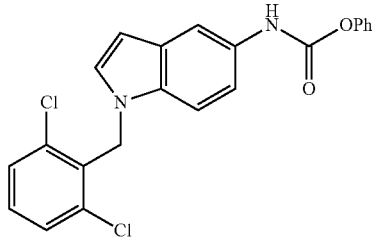

A solution of 1.18 g (7.56 mmol) of phenyl chloroformate in anhydrous dichloromethane (5 mL) was added dropwise to a solution of 2.0 g (6.87 mmol) of 5-amino-N-[(1-(2,6-dichlorophenyl)methyl]-1H-indole and 916 mg (7.56 mmol) of N,N-dimethylaniline in anhydrous dichloromethane (25 mL) under cooling on ice. Then, the mixture was stirred at room temperature for 2 hours, and the reaction mixture was diluted with water and extracted with chloroform. The organic layer was washed with 1 N hydrochloric acid, saturated sodium aqueous bicarbonate and saturated saline in this order and dried over anhydrous sodium sulfate, followed by distilling out the solvent, to give crude crystals. The resulting crude crystals were recrystallized from chloroform-hexane to give 2.55 g of the title compound (yield 90%) as pale-gray needles.

¹H-NMR (CDCl₃) δ:

5.52 (s, 2H), 6.43 (d, J=3.2 Hz, 1H), 6.92 (bs, 1H), 6.95 (d, J=3.2 Hz, 1H), 7.19-7.31 (m, 5H), 7.35-7.42 (m, 4H), 7.47 (d, J=8.9 Hz, 1H), 7.72 (bs, 1H)

EXAMPLE 8

Production of 5-phenyloxycarbonylamino-3-(1-pyrrolidinylmethyl)-N-[(1-(2,6-dichlorophenyl)methyl]-1H-indole

[Chemical formula 15]

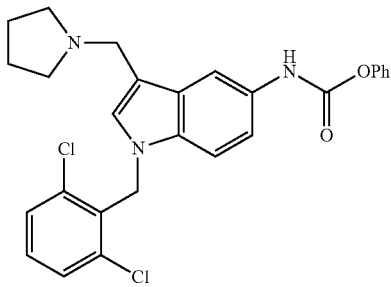

A solution of 1.20 g (2.92 mmol) of 5-phenyloxycarbonylamino-N-[(1-(2,6-dichlorophenyl)methyl]-1H-indole in methanol (15 mL) was added at room temperature to a solution of 2.07 g (29.2 mmol) of pyrrolidine, 2.80 g (46.7 mmol) of acetic acid and 1.73 g (21.3 mmol) of 37% aqueous formaldehyde in 1,4-dioxane (5 mL). Then, the mixture was stirred at room temperature for 6 hours, and then the reaction mixture was diluted with water and extracted with chloroform. The organic layer was washed with saturated saline and dried over anhydrous sodium sulfate, followed by distilling away the solvent, to give crude crystals. The resulting crude crystals were purified by silica gel chromatography (chloroform:methanol=30:1) and recrystallized from chloroformmethanol-hexane, whereby 940 mg of the title compound (yield 65%) was obtained as pale-yellow powder.

$^1$H-NMR (CDCl$_3$) δ:

1.93 (br, 2H), 2.13 (br, 2H), 2.84 (br, 2H), 3.72 (br, 2H), 4.29 (d, J=4.8 Hz, 2H), 5.55 (s, 2H), 7.15-7.43 (m, 9H), 7.44 (d, J=7.7 Hz, 1H), 7.55 (s, 1H), 7.99 (bs, 1H), 12.29 (br, 1H)

EXAMPLE 9

Production of [[N-[1-(2,6-dichlorophenyl)methyl]-3-(1-pyrrolidinylmethyl)-1H-indol-5-yl]aminocarbonyl]-glycine-N-ω-t-butoxycarbonyl-L-lysine-L-phenylalanine-N-benzhydrylamide chloroform-methanol-ether, to give 287 mg of the title compound (yield 94%) as pale-yellow solid.

$^1$H-NMR (DMSO-d$_6$, 120° C.) δ:

1.15-1.30 (m, 2H), 1.30-1.40 (m, 2H), 1.37 (s, 9H), 1.40-1.55 (m, 1H), 1.55-1.65 (m, 1H), 1.87 (br, 4H), 2.50-2.65 (m, 2H), 2.89 (overlapped with H$_2$O, 2H), 3.04 (dd, J=5.8, 13.9 Hz, 1H), 3.10 (br, 4H), 3.76 (d, J=5.3 Hz, 2H), 4.22 (dt, J=5.3, 8.0 Hz, 1H), 4.26 (s, 2H), 4.65 (dt, J=5.3, 8.0 Hz, 1H), 5.35 (s, 2H), (d, J=8.2 Hz, 2H), 6.26 (br, 1H), 7.10-7.30 (m, 15H), 7.40-7.46 (m, 2H), 7.53 (d, J=7.5 Hz, 2H), 7.61 (d, J=7.5 Hz, 1H), (d, J=8.0 Hz, 1H), 7.77 (d, J=1.9 Hz, 1H), 8.32 (d, J=8.0 Hz, 1H)

[Chemical formula 16]

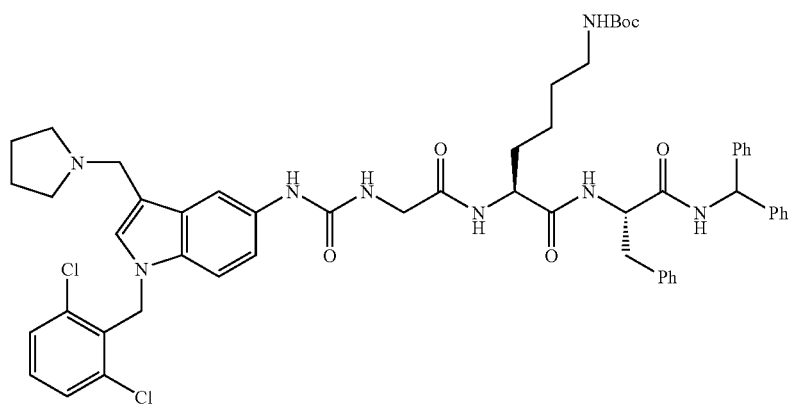

EXAMPLE 10

Production of [[N-[1-(2,6-dichlorophenyl)methyl]-3-(1-pyrrolidinylmethyl)-1H-indol-5-yl]aminocarbonyl]-glycine-L-lysine-L-phenylalanine-N-benzhydrylamide

[Chemical formula 17]

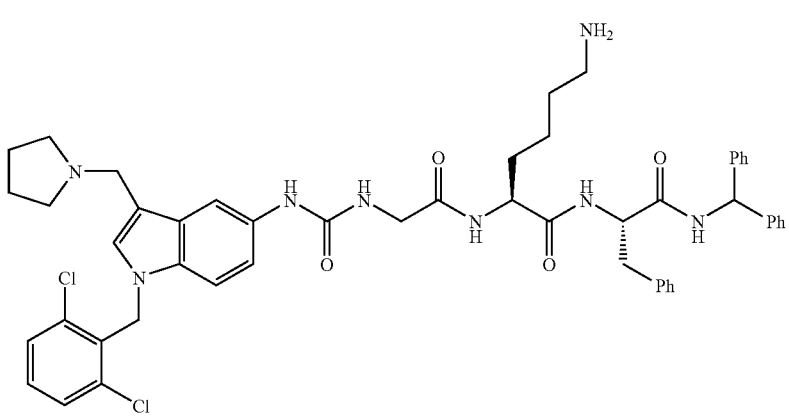

203 mg (0.33 mmol) of glycine-N-ω-t-butoxycarbonyl-L-lysine-L-phenylalanine-N-benzhydrylamide and 91 mg (0.9 mmol) of triethylamine were added to a solution of 150 mg (0.3 mmol) of 5-phenyloxycarbonylamino-3-(1-pyrrolidinylmethyl)-N-[1-(2,6-dichlorophenyl)methyl]-1H-indole in dichloroethane (20 mL). The mixture was stirred under heating at 80° C. for 3 hours and then concentrated under reduced pressure, and the resulting residues were recrystallized from 1 mL (13.15 mmol) of trifluoroacetic acid was gradually added to a solution of 34 mg (0.033 mmol) of [[N-[1-(2,6-dichlorophenyl)methyl]-3-(1-pyrrolidinylmethyl)-1H-indol-5-yl]aminocarbonyl]-glycine-N-ω-t-butoxycarbonyl-L-lysine-L-phenylalanine-N-benzhydrylamide in dichloromethane (2 mL) under cooling on ice and then stirred for 0.5 hour. 2N sodium hydroxide solution was added to the reaction mixture under cooling on ice, and then the reaction mixture was neutralized, then made basic (pH=12) and then extracted with chloroform. The organic layer was washed with saturated aqueous sodium bicarbonate water and then with saturated saline, and dried over anhydrous sodium sulfate, followed by distilling out the solvent, to give crude crystals. The resulting crude crystals were purified by silica gel chromatography and recrystallized from chloroform-methanol-ether, whereby 23 mg of the title compound (yield 75%) was obtained as pale-yellow solid.

Melting point: 207-215° C. (dec.)

$^1$H-NMR (DMSO-d$_6$, 120° C.) δ:

1.17-1.37 (m, 4H), 1.43-1.54 (m, 1H), 1.54-1.68 (m, 1H), 1.63 (br, 4H), 2.43 (br, 4H), 2.46-2.53 (m, 2H), 2.80-2.92 (m, 1H), 3.05 (dd, J=5.6, 13.9 Hz, 1H), 3.61 (s, 2H), 3.73 (d, J=4.8 Hz, 2H), 4.22 (br, 1H), 4.65 (br, 1H), 5.46 (s, 2H), 6.10 (br, 1H) 6.80 (s, 1H), 7.08-7.30 (m, 19H), 7.30 (d, J=8.7 Hz, 1H), 7.40 (dd, J=7.3, 8.8 Hz, 1H), 7.51 (d, J=7.5 Hz, 2H), 7.59 (d, J=1.9 Hz, 1H), 8.20 (br, 2H)

IR(KBr)cm-1: 3281, 1639, 1542, 1493, 1437, 699

Mass(FAB): 915, 917

EXAMPLE 11

Production of [[N-[1-(2,6-dichlorophenyl)methyl]-3-(1-pyrrolidinylmethyl)-1H-indol-5-yl]aminocarbonyl]-glycine-L-α,γ-diaminobutyrate-L-phenylalanine-N-benzhydrylamide Represented by the Following Formula The title compound was synthesized in the same manner as in Examples 1 to 10 except that L-α,γ-diaminobutyric acid was used in place of L-lysine as the amino acid moiety.

$^1$H-NMR (DMSO-d$_6$, 120° C.) δ:

1.50-1.75 (m, 2H), 1.64 (s, 4H), 2.44 (s, 4H), 2.45-2.70 (m, 2H), 3.06 (dd, J=5.8, 13.9 Hz, 1H), 3.62 (s, 2H), 3.72 (d, J=5.3 Hz, 2H), 4.33 (dd, J=5.6, 7.5 Hz, 1H), 4.65 (dd, J=5.6, 8.5 Hz, 1H), 6.08 (d, J=8.0 Hz, 1H), 6.13 (br, 1H), 6.81 (s, 2H), 7.07-7.35 (m, 20H), 7.31 (d, J=9.0 Hz, 1H), 7.40 (dd, J=7.3, 8.7 Hz, 1H), 7.50 (d, J=7.3 Hz, 2H), 8.40 (bs, 1H)

Mass(FAB): 887, 889

EXAMPLE 12

Production of [[N-[1-(2,6-dichlorophenyl)methyl]-3-[1-(4-methylpiperazinyl)methyl]-1H-indol-5-yl]aminocarbonyl]-glycine-L-lysine-L-phenylalanine-N-benzhydrylamide Represented by the Following Formula

[Chemical formula 18]

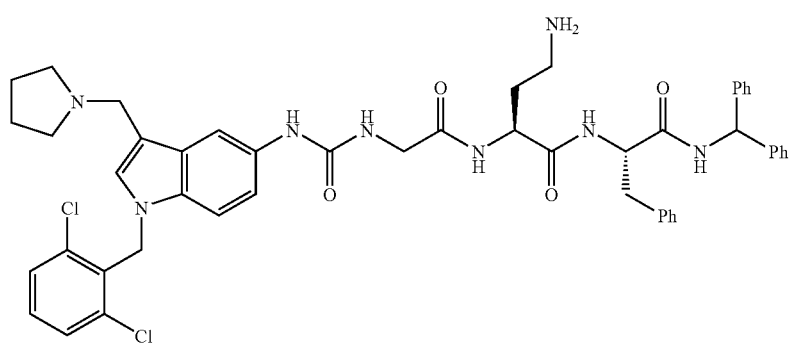

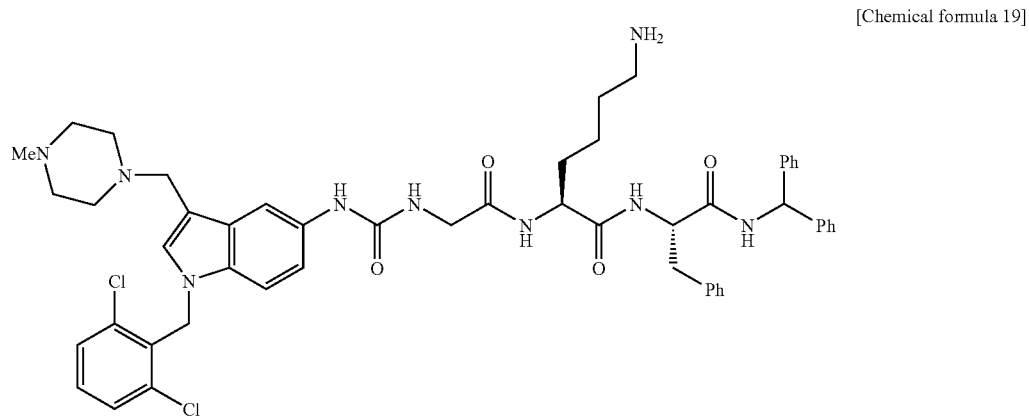

[Chemical formula 19]

In the same manner as in Example 8, a solution of 15 mg (0.036 mmol) of 5-phenyloxycarbonylamino-N-[(1-(2,6-dichlorophenyl)methyl]-1H-indole in methanol (1.0 mL) was added at room temperature to a solution of 36 mg (0.36 mmol) of 1-methylpiperazine, 35 mg (0.58 mmol) of acetic acid and 22 mg (0.27 mmol) of 37% aqueous formaldehyde in 1,4-dioxane (0.5 mL) Then, the mixture was stirred at room temperature for 16 hours and further stirred under heating at 50° C. for 2 hours, and the reaction mixture was diluted with water and extracted with chloroform. The organic layer was washed with saturated saline and dried over anhydrous sodium sulfate, followed by distilling away the solvent, to give a crude oily matter. The resulting crude oily matter was purified by silica gel chromatography (chloroform:methanol (ammonia)=40:1) to give 19 mg of 5-phenyloxycarbonylamino-3-(4-methylpiperazinyl)methyl-N-[1-(2,6-dichlorophenyl)methyl]-1H-indole (yield 100%) as colorless amorphous powder.

$^1$H-NMR (CDCl$_3$) δ:

2.24 (s, 3H), 2.30-2.65 (br, 8H), 3.61 (s, 2H), 5.47 (s, 2H), 6.88 (s, 1H), 7.05-7.35 (m, 6H), 7.35-7.45 (m, 5H), 7.75 (bs, 1H)

Subsequently, this product was used according to the same method as in Examples 9 and 10 to synthesize the title compound $^1$H-NMR (CDCl$_3$+CD$_3$OD) δ:

1.12-1.29 (m, 2H), 1.30-1.42 (m, 2H), 1.46-1.58 (m, 1H), 1.60-1.72 (m, 1H), 2.23 (s, 3H), 2.41 (bs, 4H), 2.49 (bs, 4H), 2.53-2.58 (m, 2H), 2.91-2.97 (m, 1H), 3.09-3.21 (m, 1H), 3.58 (s, 2H), 3.75 (d, J=2.1 Hz, 1H), 4.20-4.31 (m, 1H), 4.64-4.73 (m, 1H), 5.47 (s, 2H), 6.13 (s, 1H), 6.88 (s, 1H), 7.02-7.30 (m, 16H), 7.30-7.40 (m, 4H), 7.53 (d, J=1.7 Hz, 1H)

EXAMPLE 13

Production of Boc-Phe-CONHCH$_2$Ph

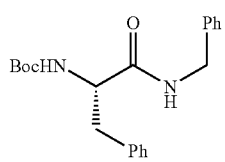

[Chemical formula 20]

2.28 g (14 mmol) of diethyl phosphorocyanidate was added to a solution of 2.65 g (10 mmol) of N-α-t-butoxycarbonyl-L-phenylalanine, 1.6 g (15 mmol) of benzyl amine and 1.8 g (14 mmol) of N,N-diisopropyl ethylamine in anhydrous tetrahydrofuran (20 mL) under cooling on ice. Then, the mixture was stirred at room temperature for 16 hours, and the reaction mixture was diluted with water and extracted with chloroform. The organic layer was washed with 1 N aqueous hydrochloric acid, saturated aqueous sodium bicarbonate and saturated saline and dried over anhydrous sodium sulfate, followed by distilling out the solvent, to give a crude oily material. The resulting crude oily material was purified by silica gel chromatography to give 3.37 g of the title compound (yield 95%) as white needles.

$^1$H-NMR (CDCl$_3$) δ:

1.39 (s, 9H), 3.05 (dd, J=7.5, 13.6 Hz, 1H), 3.11 (dd, J=6.5, 13.6 Hz, 1H), 4.28-4.41 (m, 3H), 5.02 (bs, 1H), 6.02 (bs, 1H), 7.07-7.33 (m, 10H)

EXAMPLE 14

Production of Phe-CONHCH$_2$Ph·HCl

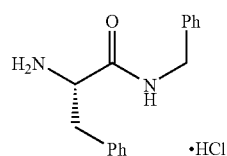

[Chemical formula 21]

10 mL (40 mmol) of 4 N hydrogen chloride in ethyl acetate was added to a solution of 2.84 g (8 mmol) of N-α-t-butoxycarbonyl-L-phenylalanine-N-benzylamide in dichloromethane (20 mL) under cooling on ice. Then, the mixture was stirred at room temperature for 3 hours and concentrated under reduced pressure, and the residues were recrystallized from chloroform-methanol-ether to give 2.3 g of the title compound (yield 98%) as white crystalline powder.

$^1$H-NMR (CD$_3$OD) δ:

3.08 (dd, J=7.3, 13.9 Hz, 1H), 3.17 (dd, J=7.3, 13.9 Hz, 1H), 4.05 (t, J=7.3 Hz, 1H), 4.27 (d, J=14.8, 1H), 4.39 (d, J=14.8, 1H), 7.11-7.16 (m, 2H), 7.21-7.35 (m, 8H)

EXAMPLE 15

Production of N-α-Fmoc-N-γ-Boc-Dab-Phe-CONHCH$_2$Ph

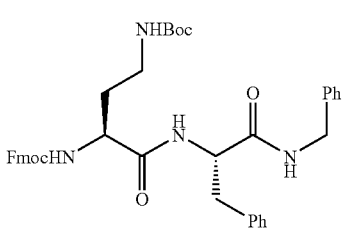

[Chemical formula 22]

By the same operation as in Example 13, 1.9 g of the title compound (yield 100%) was obtained as white crystalline powder from 1.07 g (3.7 mmol) of L-phenylalanine-N-benzylamide hydrochloride and 1.17 g (2.65 mmol) of N-α-(9-fluorenylmethoxycarbonyl)-N-γ-t-butoxycarbonyl-L-α,γ-diaminobutyric acid.

$^1$H-NMR (DMSO-d$_6$) δ:

1.37 (s, 9H), 1.60-1.71 (m, 1H), 1.73-1.84 (m, 1H), 2.90-2.95 (m, 3H), 3.01 (dd, J=6.0, 13.9 Hz, 1H), 3.04 (dd, J=5.5, 13.9 Hz, 1H), 3.95-4.06 (m, 1H), 4.12-4.32 (m, 5H), 4.58 (tt, J=6.0, 6.0 Hz, 1H), 6.11 (bs, 1H), 6.09 (bs, 1H), 7.09-7.41 (m, 8H), 7.61 (bs, 1H), 7.64 (d, J=7.5 Hz, 2H), 7.82 (d, J=7.5 Hz, 2H), 7.93 (br, 1H)

EXAMPLE 16

Production of N-γ-Boc-Dab-Phe-CONHCH₂Ph

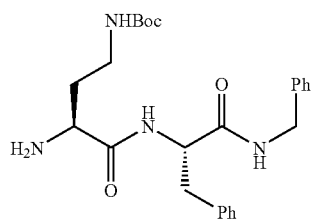

[Chemical formula 23]

10 mL (511 mmol) of diethylamine was added to a solution of 1.79 g (2.65 mmol) of [N-α-(9-fluorenylmethoxycarbonyl)]-N-γ-t-butoxycarbonyl-L-α,γ-diamonobutyrate-L-phenylalanine-N-benzylamide in tetrahydrofuran (30 mL). This mixture was stirred at room temperature for 16 hours and then concentrated under reduced pressure, and the resulting crude oily material was purified by silica gel chromatography, to give 1.19 g of the title compound (yield 98%) as white solid.

¹H-NMR (CDCl₃) δ:

1.41 (s, 9H), 1.46-1.84 (m, 2H), 3.07 (dd, J=7.5, 13.6 Hz, 2H), 3.09-3.20 (m, 2H), 3.24-3.34 (m, 1H), 4.32 (dd, J=5.3, 14.8 Hz, 1H), 4.39 (dd, J=6.0, 14.8 Hz, 1H), 4.62 (tt, J=7.5, 7.5 Hz, 1H), 4.71 (bs, 1H), 6.43 (bs, 1H), 7.09-7.30 (m, 10H), 7.87-7.96 (m, 1H)

EXAMPLE 17

Production of N-α-Fmoc-Gly-N-γ-Boc-Dab-Phe-CONHCH₂Ph

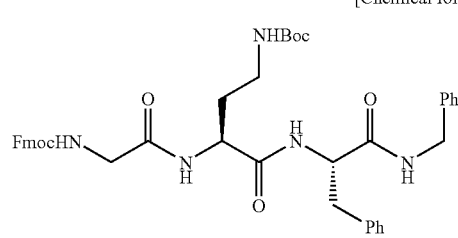

[Chemical formula 24]

By the same operation as in Example 13, 3.0 g of the title compound (yield 100%) was obtained as white solid from 1.24 g (4.18 mmol) of N-α-(9-fluorenylmethoxycarbonyl)glycine and 1.19 g (2.16 mmol) of N-γ-t-butoxycarbonyl-L-α,γ-diamonobutyrate-L-phenylalanine-N-benzylamide.

¹H-NMR (CD₃OD) δ:

1.40 (s, 9H), 1.55-1.69 (m, 1H), 1.77-1.89 (m, 1H), 2.94-3.02 (m, 3H), 3.17-3.24 (m, 1H), 3.75 (ABq, J=16.3 Hz, 2H), 4.17-4.38 (m, 6H), 4.55-4.64 (m, 1H), 7.14-7.27 (m, 10H), 7.29 (t, J=6.8 Hz, 2H), 7.38 (t, J=7.5 Hz, 2H), 7.64 (dd, J=3.4, 7.5 Hz, 2H), 7.79 (d, J=7.5 Hz, 2H)

EXAMPLE 18

Production of Gly-N-γ-Boc-Dab-Phe-CONHCH₂Ph

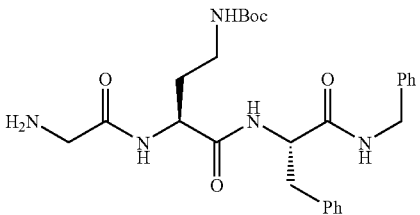

[Chemical formula 25]

By the same operation as in Example 16, 76 mg of the title compound (yield 91%) was obtained as white solid from 120 mg (0.16 mmol) of N-α-9-fluorenylmethoxycarbonylglycine-N-γ-t-butoxycarbonyl-L-α,γ-diaminobutyrate-L-phenylalanine-N-benzylamide and 2 mL (102 mmol) of diethylamine.

¹H-NMR (CDCl₃) δ:

1.37 (s, 9H), 1.45-1.70 (m, 3H), 1.88-1.98 (m, 1H), 2.81-2.96 (m, 1H), 3.09-3.22 (m, 3H), 3.21 (ABq, J=17.3 Hz, 2H), 4.32-4.46 (m, 3H), 4.70 (dt, J=6.8, 7.5 Hz, 1H), 4.83-4.93 (m, 1H), 6.93-7.02 (m, 1H), 7.14-7.29 (m, 10H), 7.67 (d, J=7.5 Hz, 1H)

EXAMPLE 19

Production of [[N-[1-(2,6-dichlorophenyl)methyl]-3-(1-pyrrolidinylmethyl)-1H-indol-5-yl]aminocarbonyl]-glycine-N-γ-t-butoxycarbonyl-L-α,γ-diaminobutyrate-L-phenylalanine-N-benzylamide Represented by the Following Formula

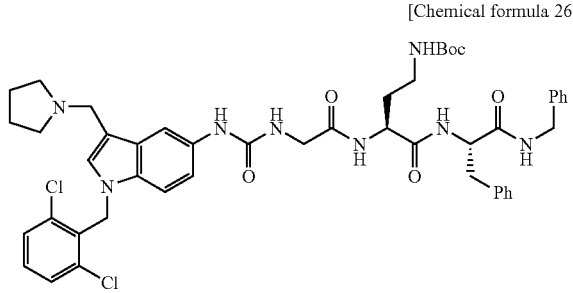

[Chemical formula 26]

56 mg (0.11 mmol) of glycine-N-γ-t-butoxycarbonyl-L-α,γ-diaminobutyrate-L-phenyl alanine-N-benzylamide and 51 mg (0.5 mmol) of triethylamine were added to a solution of 49 mg (0.1 mmol) of 5-phenyloxycarbonylamino-3-(1-pyrrolidinylmethyl)-N-[1-(2,6-dichlorophenyl)methyl]-1H-indole in dichloroethane (5 mL). This mixture was stirred at 80° C. for 3 hours and then concentrated under reduced pressure, and the resulting residues were recrystallized from chloroform-methanol-ether to give 88 mg of the title compound (yield 96%) as white crystalline powder.

¹H-NMR (DMSO-d₆, 120° C.) δ:

1.37 (s, 9H), 1.59-1.67 (m, 4H), 1.67-1.84 (m, 2H), 2.46 (bs, 4H), 2.86-2.99 (m, 2H), 3.02-3.10 (m, 1H), 3.16-3.22 (m,

1H), 3.65 (s, 2H), 3.74 (s, 2H), 4.23-4.32 (m, 3H), 4.50-4.58 (m, 1H), 5.46 (s, 2H), 6.81 (s, 1H), 7.10-7.26 (m, 12H), 7.38-7.52 (m, 4H)

EXAMPLE 20

Production of [[N-[1-(2,6-dichlorophenyl)methyl]-3-(1-pyrrolidinylmethyl)-1H-indol-5-yl]aminocarbonyl]-glycine-L-α,γ-diaminobutyrate-L-phenylalanine-N-benzylamide Represented by the Following Formula

[Chemical formula 27]

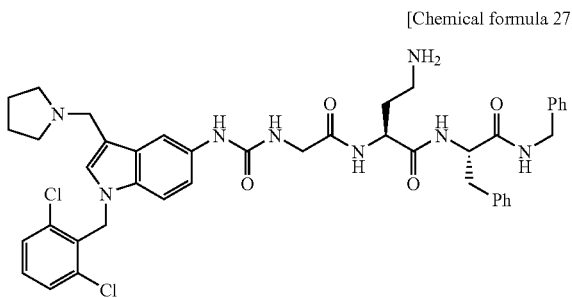

2 mL (26.3 mmol) of trifluoroacetic acid was added gradually to a solution of 160 mg (0.17 mmol) of [[N-[1-(2,6-dichlorophenyl)methyl]-3-(1-pyrrolidinylmethyl)-1H-indol-5-yl]aminocarbonyl]-glycine-N-γ-t-butoxycarbonyl-L-α,γ-diaminobutyrate-L-phenylalanine-N-benzylamide in dichloromethane (4 mL) under cooling on ice and the mixture was stirred for 0.5 hour. The reaction mixture was neutralized, then made basic (pH=12) under cooling on ice with 5 N sodium hydroxide solution and then extracted with chloroform. The organic layer was washed with saturated aqueous sodium bicarbonate and then with saturated saline, and dried over anhydrous sodium sulfate, followed by distilling out the solvent, to give crude crystals. The resulting crude crystals were purified by silica gel chromatography and recrystallized from chloroform-methanol-ether, whereby 91 mg of the title compound (yield 64%) was obtained as white crystalline powder.

Melting point: 181-188° C. (dec.)

$^1$H-NMR (DMSO-$d_6$, 120° C.) δ:

1.58-1.68 (m, 5H), 1.68-1.78 (m, 1H), 2.44 (bs, 4H), 2.50-2.80 (m, 2H), 2.80-3.12 (m, 2H), 3.62 (s, 2H), 3.74 (d, J=5.3 Hz, 2H), 4.23-4.28 (m, 2H), 4.29-4.36 (m, 1H), 4.50-4.58 (m, 1H), 5.46 (s, 2H), 6.80 (s, 1H), 7.10-7.34 (m, 12H), 7.38-7.61 (m, 4H)

IR(KBr)cm-1: 3288, 1640, 1545, 1437, 1242, 699

Mass(FAB): 811, 813

EXAMPLE 21

Production of [[N-[1-(2,6-dichlorophenyl)methyl]-3-(1-pyrrolidinylmethyl)-1H-indol-5-yl]aminocarbonyl]-glycine-L-lysine-L-phenylalanine-N-benzylamide Represented by the Following Formula

[Chemical formula 28]

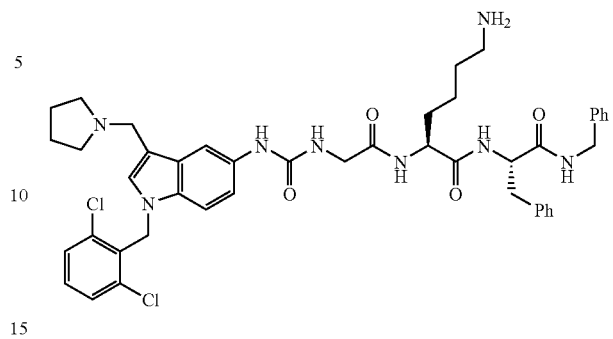

The title compound was synthesized in the same manner as in Examples 13 to 20 except that L-lysine was used in place of L-α,γ-diaminobutyric acid as the amino acid moiety.

Melting point: 188-192° C. (dec.)

$^1$H-NMR (DMSO-$d_6$, 120° C.) δ:

1.20-1.38 (m, 4H), 1.44-1.55 (m, 1H), 1.56-1.67 (m, 1H), 1.63 (br, 4H), 2.43 (br, 4H), 2.52 (t, J=6.5 Hz, 2H), 2.88 (dd, J=8.5, 13.9 Hz, 1H), 3.06 (dd, J=5.8, 13.9 Hz, 1H), 3.62 (s, 2H), 3.75 (d, J=5.3 Hz, 2H), 4.21 (br, 1H), 4.25 (t, J=5.8 Hz, 2H), 4.54 (br, 1H), 5.46 (s, 2H), 6.11 (br, 1H), 6.80 (s, 1H), 7.83 (br, 1H), 7.10 (m, 12H), 7.31 (d, J=8.7 Hz, 1H), 7.40 (dd, J=7.3, 8.7 Hz, 1H), 7.49-7.60 (m, 2H), 7.59 (d, J=1.7 Hz, 1H), 7.83 (br, 1H), 8.21 (bs, 1H)

IR(KBr)cm-1: 3288, 1639, 1546, 1487, 1454, 1437, 699

Mass(FAB): 839, 841

EXAMPLE 22

Production of [[N-[1-(2,6-dichlorophenyl)methyl]-3-(1-pyrrolidinylmethyl)-1H-indol-5-yl]aminocarbonyl]-glycine-L-α,γ-diaminobutyrate-L-valine-N-benzylamide Represented by the Following Formula

[Chemical formula 29]

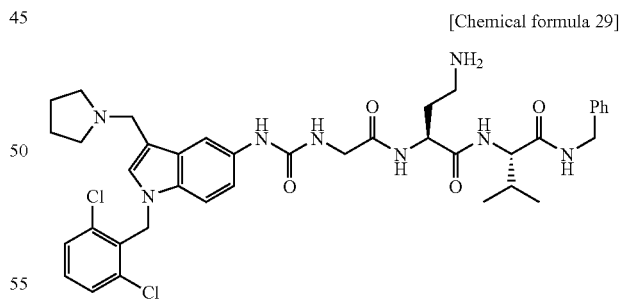

The title compound was synthesized in the same manner as in Examples 13 to 20 except that L-valine was used in place of L-phenylalanine as the amino acid moiety.

$^1$H-NMR (DMSO-$d_6$, 120° C.) δ:

0.85 (d, J=6.8 Hz, 3H), 0.86 (d, J=6.8 Hz, 3H), 1.64 (brs, 4H), 1.64-1.85 (m, 2H), 2.03 (qq, J=6.8, 6.8 Hz, 1H), 2.44 (bs, 4H), 2.60-2.66 (m, 2H), 3.62 (s, 2H), 3.75 (s, 2H), 4.13-4.18 (m, 1H), 4.23-4.30 (m, 2H), 4.39-4.45 (m, 1H), 5.46 (s, 2H), 6.80 (s, 1H), 7.10-7.60 (m, 11H)

EXAMPLE 23

Production of [[N-[1-(2,6-dichlorophenyl)methyl]-1H-indol-5-yl]aminocarbonyl]-glycine-L-α,γ-diaminobutyrate-L-phenylalanine-N-benzylamide Represented by the Following Formula

[Chemical formula 30]

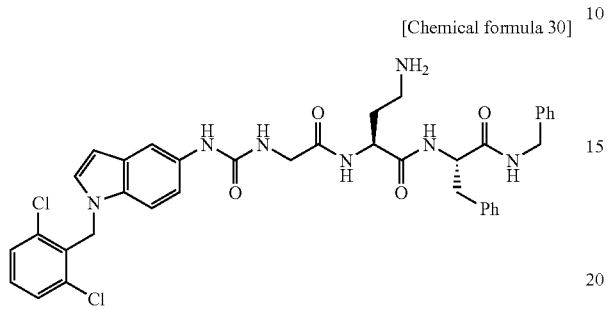

The title compound was synthesized in the same manner as in Examples 13 to 20 except that 5-phenyloxycarbonylamino-N-[1-(2,6-dichlorophenyl)methyl]-1H-indole was used in place of 5-phenyloxycarbonylamino-3-(1-pyrrolidinylmethyl)-N-[(1-(2,6-dichlorophenyl)methyl]-1H-indole as the indole ring moiety.

$^1$H-NMR (DMSO-$d_6$) δ:
1.55-1.66 (m, 1H), 1.67-1.77 (m, 1H), 2.48-2.46 (m, 2H), 2.85-3.14 (m, 2H), 3.73 (d, J=5.3 Hz, 2H), 4.20-4.28 (m, 2H), 4.29-4.35 (m, 1H), 4.53-4.59 (m, 1H), 5.49 (s, 2H), 6.16 (br, 1H), 6.29 (d, J=3.1 Hz, 1H), 6.90 (d, J=3.1 Hz, 1H), 7.10-7.28 (m, 11H), 7.32-7.58 (m, 5H), 7.86 (bs, 1H)

EXAMPLE 24

Production of [[N-isopropyl-1H-indol-5-yl]aminocarbonyl]-glycine-L-α,γ-diaminobutyrate-L-phenylalanine-N-benzylamide Represented by the Following Formula

[Chemical formula 31]

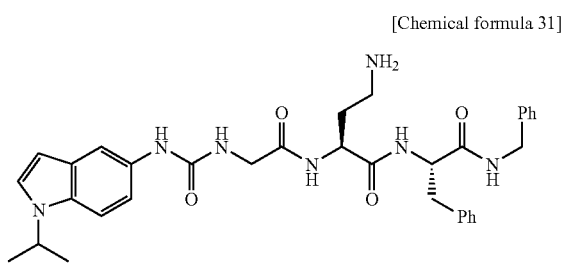

The title compound was synthesized in the same manner as in Examples 13 to 20 except that 5-phenyloxycarbonylamino-N-isopropyl-1H-indole was used in place of 5-phenyloxycarbonylamino-3-(1-pyrrolidinylmethyl)-N-[(1-(2,6-dichlorophenyl)methyl]-1H-indole as the indole ring moiety.

$^1$H-NMR (DMSO-$d_6$, 120° C.) δ:
1.44 (d, J=6.3 Hz, 6H), 1.50-1.63 (m, 1H), 1.63-1.75 (m, 1H), 2.45-2.60 (m, 2H), 2.90-3.25 (m, 2H), 3.72 (bs, 2H), 4.25 (bs, 2H), 4.25-4.45 (m, 1H), 4.50-4.60 (m, 1H), 4.60- 4.75 (m, 1H), 6.13 (bs, 1H), 6.30 (bs, 1H), 7.02-7.35 (m, 13H), 7.55 (bs, 1H), 7.85 (br, 1H)

EXAMPLE 25

Production of [[N-isopropyl-1H-indol-5-yl]aminocarbonyl]-L-alanine-L-α,γ-diaminobutyrate-L-phenylalanine-N-benzylamide Represented by the Following Formula

[Chemical formula 32]

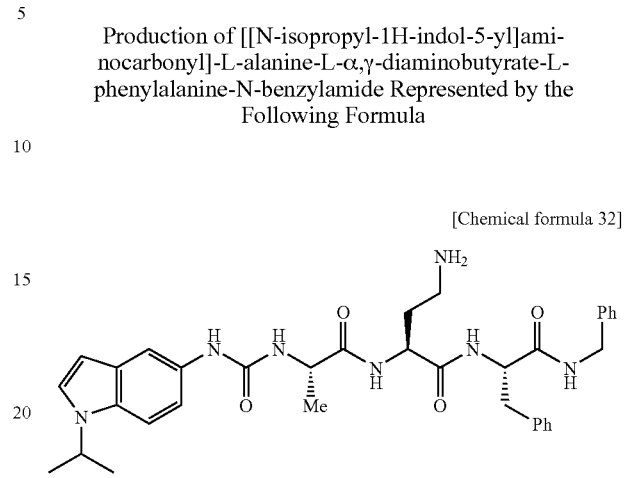

The title compound was synthesized in the same manner as in Example 24 except that L-alanine was used in place of glycine as the amino acid moiety.

$^1$H-NMR (CDCl$_3$+CD$_3$OD) δ:
1.29 (d, J=7.3 Hz, 3H), 1.46 (d, J=6.5 Hz, 3H), 1.49 (d, J=6.5 Hz, 3H), 1.59-1.67 (m, 2H), 1.87-1.99 (m, 1H), 2.40-2.50 (m, 1H), (dd, J=10.9, 14.1 Hz, 1H), 3.35 (dd, J=4.6, 14.1 Hz, 1H), 3.94 (q, J=7.3 Hz, 1H), 4.22-4.29 (m, 1H), 4.44 (ABq, J=15.1 Hz, 2H), 4.61 (qq, J=6.5, 6.5 Hz, 1H), 4.77 (dd, J=4.6, 10.9 Hz, 1H), 6.44 (d, J=3.1 Hz, 1H), 6.88-7.07 (m, 5H), 7.16 (dd, J=1.9, 8.7 Hz, 1H), 7.23 (d, J=3.1 Hz, 1H), 7.23-7.37 (m, 6H), 7.54 (d, J=1.9 Hz, 1H)

EXAMPLE 26

Production of [[N-isopropyl-1H-indol-5-yl]aminocarbonyl]-(β-cyclohexyl-L-alanine)-L-α,γ-diaminobutyrate-L-phenylalanine-N-benzylamide Represented by the Following Formula

[Chemical formula 32]

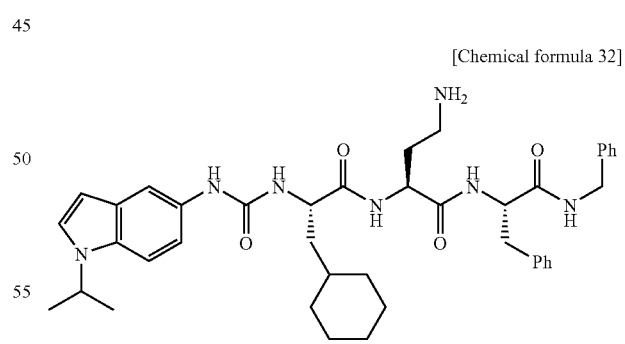

The title compound was synthesized in the same manner as in Example 24 except that β-cyclohexyl-L-alanine was used in place of glycine as the amino acid moiety.

$^1$H-NMR (CDCl$_3$+CD$_3$OD) δ:
0.80-1.00 (m, 2H), 1.12-1.38 (m, 7H), 1.46 (d, J=6.8 Hz, 3H), 1.49 (d, J=6.8 Hz, 3H), 1.60-1.78 (m, 6H), 2.00-2.12 (m, 1H), 2.40-2.50 (m, 1H), 2.86 (dd, J=10.9, 14.1 Hz, 1H), 3.33 (dd, J=4.6, 14.1 Hz, 1H), 3.98 (tt, J=4.3, 4.6 Hz, 1H), 4.22-4.28 (m, 1H), 4.46 (ABq, J=15.1 Hz, 2H), 4.61 (qq, J=6.8, 6.8

Hz, 1H), 4.75 (dd, J=4.6, 10.9 Hz, 1H), 6.44 (d, J=3.1 Hz, 1H), 6.87-7.08 (m, 5H), 7.18 (dd, J=1.9, 8.7 Hz, 1H), 7.23 (d, J=3.1 Hz, 1H), 7.26 (m, 6H), 7.54 (d, J=1.9 Hz, 1H)

EXAMPLE 27

Production of [[N-[1-(2,6-dichlorophenyl)methyl]-3-(1-pyrrolidinylmethyl)-1H-indol-5-yl]aminocarbonyl]-glycine-L-α,γ-diaminobutyrate-[3-(2-naphthyl)-L-alanine]-N-benzylamide Represented by the Following Formula

[Chemical formula 34]

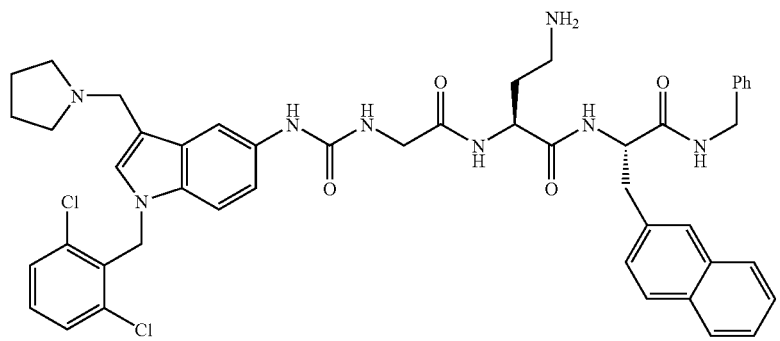

The title compound was synthesized in the same manner as in Examples 13 to 20 except that 3-(2-naphthyl)-L-alanine was used in place of L-phenylalanine as the amino acid moiety.

$^1$H-NMR (DMSO-$d_6$, 120° C.) δ:
1.55-1.57 (m, 2H), 1.63 (bs, 4H), 2.43 (bs, 4H), 2.40-2.46 (m, 2H), 3.07 (dd, J=8.2, 13.8 Hz, 1H), 3.25 (dd, J=8.2, 13.8 Hz, 1H), 3.26 (s, 2H), 3.70 (d, J=5.3 Hz, 2H), 4.26 (dd, J=5.8, 8.2 Hz, 2H), 4.33 (dd, J=5.8, 7.4 Hz, 1H), 4.66 (dd, J=5.8, 8.2 Hz, 2H), 5.45 (s, 2H), 6.15 (br, 1H), 6.80 (s, 1H), 7.10-7.25 (m, 6H), 7.27-7.35 (m, 2H), 7.35-7.45 (m, 3H), 7.49 (d, J=8.2 Hz, 2H), 7.62 (d, J=8.4 Hz, 2H), 7.72 (d, J=8.4 Hz, 2H), 7.75-7.82 (m, 1H), 7.91 (br, 1H), 8.23 (bs, 1H)

TEST EXAMPLE 1

Assay of Intracellular $Ca^{2+}$ Level

In this test, the compound in Example 10 was used as PAR-2 antagonist, and SLIGKV (SEQ ID NO: 3) (expressed in single letter amino acid code and the same in the following) or SLIGRL (SEQ ID NO: 4) (confirmed to have a purity of 95% or more by HPLC, the synthesis of which was entrusted to Peptide Institute, Inc. (Osaka, Japan), were diluted in a keratinocyte basal medium (referred to hereinafter as KBM) and used as PAR-2 agonist peptides as stimulants respectively. Human keratinocytes used were obtained from Bio-Whicker and cultured in a keratinocyte culture medium (hereinafter referred to as KGM-2). The keratinocytes were subjected to passage culture with trypsin/EDTA, and the cells whose passage number was 3 to 5 were used in the experiment.

Flex Station Calcium assay kit 2, which is a fluorescent reagent kit for calcium assay, was purchased from Molecular Devices and used in reagent preparation according to an accompanying protocol. Probenecid, Calcium ionophore (A23187) was purchased from Sigma. The human keratinocytes were seeded at a density of 40,000 cells/well to a 96-well black-well clear-bottom plate (Corning) and cultured for 24 hours until the cells became subconfluent. After washing once with KBM, 80 μl KBM was added to each well. Subsequently, a fluorescent dye solution containing an equal volume of Probenecid at a final concentration of 2 mM (HBSS solution, pH 7.4) was added to each well and incubated at 37° C. for 1 hour. Thereafter, the plate was left for 15 minutes at room temperature and assayed at room temperature (25° C.). The test chemical and the stimulants were prepared by diluting KBM having 10-fold concentration of a final concentration respectively which were then added in a volume of 20 μL respectively for assay. Measurement was carried out with a fluorescent plate reader FlexStation (Molecular Devices) compatible with a 96-well plate equipped with an injector. The measurement through the bottom was carried out for 180 seconds at 2-second intervals at an excitation wavelength of 475 nm and at a measurement wavelength of 525 nm. The chemical was added 17 seconds after the measurement was initiated.

The results are shown in FIG. 1. When the cultured human keratinocytes were stimulated with the PAR-2 agonist (SLIGKV (SEQ ID NO: 3), final concentration of 10 μM), a transient increase in intracellular $Ca^{2+}$ level was observed (control). On the other hand, when the compound in Example 10 (final concentration of 10 μg/mL) was added, inhibition was recognized.

From FIG. 1, the inhibition rate with the antagonist (1-AUC$_{antagonist}$/AUC$_{control}$))×100(%) was calculated from the ratio of the area under the (time-fluorescence intensity) curve (AUC$_{antagonist}$) in the presence of the compound in Example 10 to the area under the (time-fluorescence intensity) curve (AUC$_{control}$) for an intracellular $Ca^{2+}$ level change when the agonist was added alone (control), and as a result, the inhibition rate with the compound in Example 10 in this experiment was 58.4±13.0 (means±standard error)%(n=3).

Similarly, the degrees of inhibition with the compounds (at a final concentration of 10 μg/mL) in Examples 11, 12, 20, 21 and 24 were calculated. The degrees of inhibition with the respective compounds, together with the result of the compound in Example 10, are shown in Table 1.

TABLE 1

| Example No. | Inhibition Rate (%) (Means ± Standard Error, n = 3) |
|---|---|
| 10 | 58.4 ± 13.0 |
| 11 | 32.0 ± 2.3 |
| 12 | 52.2 ± 1.8 |

TABLE 1-continued

| Example No. | Inhibition Rate (%) (Means ± Standard Error, n = 3) |
|---|---|
| 20 | 33.6 ± 16.8 |
| 21 | 14.2 ± 10.0 |
| 24 | 15.1 ± 10.5 |

Any compounds in the Examples were revealed to have an evident PAR-2 inhibitory action.

INDUSTRIAL APPLICABILITY

According to the present invention, there can be provided a PAR-2 antagonist acting competitively on a ligand-binding site of receptor thereby inhibiting the activation of the PAR-2 accurately at the receptor level. Further, there can be provided a pharmaceutical preparation useful for prevention of development and progress, amelioration of clinical state, treatment or the like for PAR-2-associated diseases, for example, respiratory diseases such as asthma, allergic diseases such as allergic rhinitis, cardiovascular system diseases such as myocardial infarction, nervous system diseases such as neuralgia, inflammatory diseases such as atopic dermatitis and chronic arthritis, and cancers.

The invention claimed is:

1. A compound represented by the general formula (1) or a salt thereof:

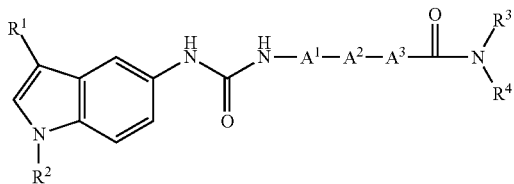

(1)

wherein $R^1$ represents a hydrogen atom, a halogen atom, or a group represented by the following formula (2):

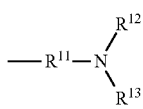

(2)

wherein $R^{11}$ represents a $C_1$ to $C_6$ straight-chain or branched alkylene group, $R^{12}$ and $R^{13}$ together with the nitrogen atom adjacent to them form a 5- to 7-member ring structure, 1 to 2 carbon atoms in the ring may be substituted with a nitrogen atom or an oxygen atom, and the ring may be substituted with a $C_1$ to $C_6$ straight-chain or branched alkyl group;

$R^2$ represents a $C_1$ to $C_6$ straight-chain or branched alkyl group, a $C_3$ to $C_6$ cycloalkyl group, a $C_1$ to $C_6$ straight-chain or branched alkyl group substituted with a $C_3$ to $C_6$ cycloalkyl group, or a $C_7$ to $C_{12}$ aralkyl group which may be substituted with 1 to 3 halogen atoms or with a $C_1$ to $C_6$ straight-chain or branched alkyl group;

each of $R^3$ and $R^4$ independently represents a hydrogen atom or a $C_7$ to $C_{21}$ aralkyl group which may be substituted with 1 to 3 halogen atoms or with a $C_1$ to $C_6$ straight-chain or branched alkyl group;

$A^1$ represents an α-amino acid selected from the group consisting of glycine, alanine and cyclohexylalanine;

$A^2$ represents an α-amino acid selected from the group consisting of α,γ-diaminobutyric acid and lysine; and $A^3$ represents an α-amino acid selected from the group consisting of phenylalanine, valine, and β-naphthylalanine.

2. The compound or salt thereof according to claim 1, wherein said compound is selected from the group consisting of:

[[N-[1-(2,6-dichlorophenyl)methyl]-3-(1-pyrrolidinylmethyl)-1H-indol-5-yl]aminocarbonyl]-glycine-L-lysine-L-phenylalanine-N-benzhydrylamide,

[[N-[1-(2,6-dichlorophenyl)methyl]-3-(1-pyrrolidinylmethyl)-1H-indol-5-yl]aminocarbonyl]-glycine-L-α,γ-diaminobutyrate-L-phenylalanine-N-benzhydrylamide,

[[N-[1-(2,6-dichlorophenyl)methyl]-3-[1-(4-methylpiperazinyl)methyl]-1H-indol-5-yl]aminocarbonyl]-glycine-L-lysine-L-phenylalanine-N-benzhydrylamide,

[[N-[1-(2,6-dichlorophenyl)methyl]-3-(1-pyrrolidinylmethyl)-1H-indol-5-yl]aminocarbonyl]-glycine-L-α,γ-diaminobutyrate-L-phenylalanine-N-benzylamide,

[[N-[1-(2,6-dichlorophenyl)methyl]-3-(1-pyrrolidinylmethyl)-1H-indol-5-yl]aminocarbonyl]-glycine-L-lysine-L-phenylalanine-N-benzylamide,

[[N-[1-(2,6-dichlorophenyl)methyl]-3-(1-pyrrolidinylmethyl)-1H-indol-5-yl]aminocarbonyl]-glycine-L-α,γ-diaminobutyrate-L-valine-N-benzylamide,

[[N-[1-(2,6-dichlorophenyl)methyl]-1H-indol-5-yl]aminocarbonyl]-glycine-L-α,δ-diaminobutyrate-L-phenylalanine-N-benzylamide,

[[N-isopropyl-1H-indol-5-yl]aminocarbonyl]-glycine-L-α,γ-diaminobutyrate-L-phenylalanine-N-benzylamide,

[[N-isopropyl-1H-indol-5-yl]aminocarbonyl]-L-alanine-L-α,γ-diaminobutyrate-L-phenylalanine-N-benzylamide,

[[N-isopropyl-1H-indol-5-yl]aminocarbonyl]-(β-cyclohexyl-L-alanine)-L-α,γ-diaminobutyrate-L-phenylalanine-N-benzylamide, and

[[N-[1-(2,6-dichlorophenyl)methyl]-3-(1-pyrrolidinylmethyl)-1H-indol-5-yl]aminocarbonyl]-glycine-L-α,γ-diaminobutyrate-[3-(2-naphthyl)-L-alanine]-N-benzylamide.

3. A compound represented by the general formula (3) or a salt thereof:

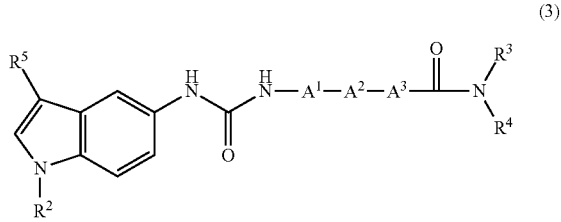

(3)

wherein $R^5$ represents a halogen atom or —CO—$R^{51}$ where $R^{51}$ represents a hydrogen atom, a $C_1$ to $C_6$ straight-chain or branched alkyl group, an optionally substituted phenyl group or an optionally substituted 2-furoyl group;

$R^2$ represents a $C_1$ to $C_6$ straight-chain or branched alkyl group, a $C_3$ to $C_6$ cycloalkyl group, a $C_1$ to $C_6$ straight-chain or branched alkyl group substituted with a $C_3$ to $C_6$ cycloalkyl group, or a $C_7$ to $C_{12}$ aralkyl group which may be substituted with 1 to 3 halogen atoms or with a $C_1$ to $C_6$ straight-chain or branched alkyl group;

each of $R^3$ and $R^4$ independently represents a hydrogen atom or a $C_7$ to $C_{21}$ aralkyl group which may be substituted with 1 to 3 halogen atoms or with a $C_1$ to $C_6$ straight-chain or branched alkyl group;

$A^1$ represents an α-amino acid selected from the group consisting of glycine, alanine and cyclohexylalanine;

$A^2$ represents an α-amino acid selected from the group consisting of α,γ-diaminobutyric acid and lysine; and $A^3$ represents an α-amino acid selected from the group consisting of phenylalanine, valine, and β-naphthylalanine.

* * * * *

```
                         SEQUENCE LISTING

<160> NUMBER OF SEQ ID NOS: 4

<210> SEQ ID NO 1
<211> LENGTH: 6
<212> TYPE: PRT
<213> ORGANISM: Artificial
<220> FEATURE:
<221> NAME/KEY: Ornithine
<222> LOCATION: (6)...(6)
<223> OTHER INFORMATION: Chemically synthesized peptides

<400> SEQUENCE: 1

Leu Ile Gly Arg Leu Xaa
1               5

<210> SEQ ID NO 2
<211> LENGTH: 5
<212> TYPE: PRT
<213> ORGANISM: Artificial
<220> FEATURE:
<223> OTHER INFORMATION: Chemically synthesized peptides

<400> SEQUENCE: 2

Leu Ile Gly Arg Leu
1               5

<210> SEQ ID NO 3
<211> LENGTH: 6
<212> TYPE: PRT
<213> ORGANISM: Artificial
<220> FEATURE:
<223> OTHER INFORMATION: Chemically synthesized peptides

<400> SEQUENCE: 3

Ser Leu Ile Gly Lys Val
1               5

<210> SEQ ID NO 4
<211> LENGTH: 6
<212> TYPE: PRT
<213> ORGANISM: Artificial
<220> FEATURE:
<223> OTHER INFORMATION: Chemically synthesized peptides

<400> SEQUENCE: 4

Ser Leu Ile Gly Arg Leu
1               5
```